US012365923B2

(12) United States Patent
Nakada et al.

(10) Patent No.: US 12,365,923 B2
(45) Date of Patent: Jul. 22, 2025

(54) METHOD FOR PRODUCING GENOME-EDITED CELL

(71) Applicant: OSAKA UNIVERSITY, Suita (JP)

(72) Inventors: Shinichiro Nakada, Suita (JP); Akiko Tomita, Suita (JP)

(73) Assignee: OSAKA UNIVERSITY, Suita (JP)

( * ) Notice: Subject to any disclaimer, the term of this patent is extended or adjusted under 35 U.S.C. 154(b) by 1067 days.

(21) Appl. No.: 17/294,165

(22) PCT Filed: Aug. 7, 2019

(86) PCT No.: PCT/JP2019/031117

§ 371 (c)(1),
(2) Date: May 14, 2021

(87) PCT Pub. No.: WO2020/100361

PCT Pub. Date: May 22, 2020

(65) Prior Publication Data

US 2021/0324420 A1 Oct. 21, 2021

(30) Foreign Application Priority Data

Nov. 16, 2018 (JP) ................................ 2018-215588

(51) Int. Cl.
*C12N 15/90* (2006.01)
*C12N 9/22* (2006.01)
*C12N 15/11* (2006.01)

(52) U.S. Cl.
CPC ............ *C12N 15/907* (2013.01); *C12N 9/22* (2013.01); *C12N 15/11* (2013.01); *C12N 2310/20* (2017.05); *C12N 2800/80* (2013.01)

(58) Field of Classification Search
CPC ........ C12N 15/907; C12N 9/22; C12N 15/11; C12N 2310/20; C12N 2800/80; C12N 15/90; C12N 15/102
See application file for complete search history.

(56) References Cited

U.S. PATENT DOCUMENTS

2016/0153005 A1 6/2016 Zhang et al.
2019/0233846 A1* 8/2019 Feng .................... C12N 5/0603

FOREIGN PATENT DOCUMENTS

JP 2018-011525 A 1/2018
WO 2014/065596 A1 5/2014
WO 2017/044419 A1 3/2017

OTHER PUBLICATIONS

Wu, Y. et al. "Correction of a genetic disease in mouse via use of CRISPR-Cas9". Cell Stem Cell, vol. 13 (2013), pp. 659-662 (Year: 2013).*

Trevino, A.E. et al. "Genome editing using Cas9 nickases". Methods in Enzymology, vol. 546 (2014), pp. 161-174. (Year: 2014).*

Gonçalves, M.A.F.V. et al."Concerted nicking of donor and chromosomal acceptor DNA promotes homology-directed gene targeting in human cells". Nucleic Acids Research, vol. 40, No. 8 (2012), pp. 3443-3455 (Year: 2012).*

Jiang, S. et al. CRISPR/Cas9-mediated genome editing in Epstein-Barr virus-transformed lymphoblastoid B-cell lines. Current Protocols in Molecular Biology, vol. 121 (Jan. 2018), pp. 31.12.1-31.12.23. (Year: 2018).*

Vriend, L.E.M. et al. "Distinct genetic control of homologous recombination repair of Cas9-induced double-strand breaks, nicks and paired nicks." Nucleic Acids Research, vol. 44, No. 11 (2016), pp. 5204-5217. (Year: 2016).*

Communication, dated May 27, 2021, issued by the International Bureau in International Application No. PCT/JP2019/031117.

Extended European Search Report, dated Feb. 2, 2022, issued by the European Patent Office in European Application No. 19885454.9.

Cory Smith et al., "Efficient and Allele-Specific Genome Editing of Disease Loci in Human iPSCs", Molecular Therapy, 2015, vol. 23, No. 3, pp. 570-577 (8 pages total).

Cherie L. Ramirez et al., "Engineered zinc finger nickases induce homology-directed repair with reduced mutagenic effects", Nucleic Acids Research, 2012, vol. 40, No. 12, pp. 5560-5568 (9 pages total).

Jianbin Wang et al., "Targeted gene addition to a predetermined site in the human genome using a ZFN-based nicking enzyme", Genome Res., 2012, vol. 22, No. 7, pp. 1316-1326 (12 pages total).

Eunji Kim et al., "Precision genome engineering with programmable DNA-nicking enzymes", Genome Research, 2012, vol. 22, No. 7, pp. 1327-1333 (7 pages total).

A.V. Smirnov et al., "CRISPR/Cas9, a Universal Tool for Genomic Engineering", Russian Journal of Genetics: Applied Research, 2017, vol. 7, No. 4, pp. 440-458 (19 pages total).

Alexis C. Komor et al., "CRISPR-Based Technologies for the Manipulation of Eukaryotic Genomes", Cell, 2017, vol. 168, No. 1, pp. 20-36 (17 pages total).

Yuxuan Wu et al., "Correction of a Genetic Disease in Mouse via Use of CRISPR-Cas9", Cell Stem Cell, Dec. 5, 2013, pp. 659-662, vol. 13.

Kazuhiro Nakajima et al., "Precise and efficient nucleotide substitution near genomic nick via noncanonical homology-directed repair", Genome Research, Nov. 27, 2017, pp. 223-230.

International Search Report of PCT/JP2019/031117, dated Oct. 15, 2019 [PCT/ISA/210].

* cited by examiner

*Primary Examiner* — Anna Skibinsky
*Assistant Examiner* — Alexandra Geraldine Dace Denito
(74) *Attorney, Agent, or Firm* — Sughrue Mion, PLLC

(57) ABSTRACT

Nicks were generated at multiple sites in the neighboring DNA region of the nucleotide to be modified on the recipient chromosome, and on the donor chromosome, a nick was generated at at least one site corresponding to the site where a nick was to be generated on the recipient chromosome. Thereby, the present inventors have succeeded in significantly suppressing non-homologous end joining and specifically inducing recombination between homologous chromosomes at the target site.

6 Claims, 28 Drawing Sheets

Specification includes a Sequence Listing.

Fig. 2A

SEQ ID NO: 1 gtgtctcgctgtgttacccaggctggtctcgaactcctgagttcaagtgatcctcccgtcttggcctcc
ccaaagattacgggcatgagctgctgtgtctggccagaatacaggattttaaaatttatgttttgcaa
cataattaatataaagacaaatataacccaggcccagttctagttattcattcttctgaattttaaaag
gaaacatttggctggcccctaatggtatcatgggccctggtacctgatgaagttggcctagtctgcccc
cagctcctgaacagtggaagagtttttagtctcattgagctttgtactggacattactaatttctaatc
caaagcatcaagtgaagtggcttgtataaataactggttttcctctgggaggctaaggcgggtggatca
cttaaaagttaggagtctgagaccagcctggccaacatggtgaaaccccatgtctgctaaaaatacaaa
aattagctgggtgtgatggtgtgtgccagtagtcccagctactcttgtggctgaggtgggagaatcgct
tgagacccttgagaattgggaggtagagattgcagggagccgagatggcgccactgcactccagcctgg
gtgacagagcaagactctgtttcataaaaataaataaataactggttttctggacgagggcctttccc
ataggtgctaacttctcaaagcccggctgggtgaacactgagcctgctttgcaggtagcaggtggtcac
gacagtgccattccctggcccctgcattgtggcttctggcctccctggccctgctcacgctctggcttt
ctcttcccagGAACACCATGGAGGCACTGCCCGCCTGCCTGCTCCGAGACGTGGCCCAGGAGGCCCTGG
GCGTGGCTGTCATAGGCATCGACGAGGGGCAGTTTgtaagttggcttgtcttggcatcactcttcctgc
cagcttccgctctgtcctcccgttttccctcgctgacttggaagttatctgatcttttagtaaaataac
aaggttaaatagctacaactagtgttggaataccctctgaaggcccctttctagtttccctgtcatagt
gtcatagtcttgtaggattcgtttacttttttttttttttttgagacggagttttgctcttgttgc
ccaggccggagtacgatggcacaatctcaccgcaaactttgcttcctgggttcaagcaattctctcctg
tctcagcctcccgagtagctgggattacaggcatgcgccaccacgcccagctaattttatatttttagt
agagatggggtttctccatgttggtcaagctggtctcaaactcccaacctcaggtgatccgccccgcct
tgaactcccaaagcgctgggattacaggcatgagctaccacacctggccattgtacctttttaaaaata
catatatctatttactggcaagatgcagtgactcacacctgtaatctcagcctgtgggaggccaaggtg
gacagatcacttgagcccagga

Fig. 2B

SEQ ID NO: 2 gtgtctcgctgtgttacccaggctggtctcgaactcctgagttcaagtgatcctcccgtcttggcctcc
ccaaagattacgggcatgagctgctgtgtctggccagaatacaggattttaaaaatttatgttttgcaa
cataattaatataaagacaaatataacccaggcccagttctagttattcattcttctgaattttaaaag
gaaacatttggctggcccctaatggtatcatgggccctggtacctgatgaagttggcctagtctgcccc
cagctcctgaacagtggaagagttttagtctcattgagctttgtactggacattactaatttctaatc
caaagcatcaagtgaagtggcttgtataaataactggttttcctctgggaggctaaggcgggtggatca
cttaaaagttaggagtctgagaccagcctggccaacatggtgaaaccccatgtctgctaaaaatacaaa
aattagctgggtgtgatggtgtgtgccagtagtcccagctactcttgtggctgaggtgggagaatcgct
tgagacccttgagaattgggaggtagagattgcagggagccgagatggcgccactgcactccagcctgg
gtgacagagcaagactctgtttcataaaaaataaataaataactggttttctggacgagggcctttccc
ataggtgctaacttctcaaagcccggctgggtgaacactgagcctgctttgcaggtagcaggtggtcac
gacagtgccattccctggcccctgcattgtggcttctggcctccctggccctgctcacgctctggcttt
ctcttcccagGAACACCATGGAGGCACTGCCC*CGCCTGCCTGCTCCGAGACGTGGCCCAGGAGGCCCTG
GGCGTGGCTGTCATAGGCATCGACGAGGGGCAGTTTgtaagttggcttgtcttggcatcactcttcctg
ccagcttccgctctgtcctcccgttttccctcgctgacttggaagttatctgatcttttagtaaaataa
caaggttaaatagctacaactagtgttggaataccctctgaaggcccctttctagtttccctgtcatag
tgtcatagtcttgtaggattcgttttactttttttttttttttttgagacggagttttgctcttgttg
cccaggccggagtacgatggcacaatctcaccgcaaactttgcttcctgggttcaagcaattctctcct
gtctcagcctcccgagtagctgggattacaggcatgcgccaccacgcccagctaattttatatttttag
tagagatggggtttctccatgttggtcaagctggtctcaaactcccaacctcaggtgatccgccccgcc
ttgaactcccaaagcgctgggattacaggcatgagctaccacacctggccattgtacctttttaaaaat
acatatatctatttactggcaagatgcagtgactcacacctgtaatctcagcctgtgggaggccaaggt
ggacagatcacttgagcccagga

Fig. 2C

S 1 (SEQ ID NO: 3)

TACTGATTCTCCAGCTCCTGCAGGGCACAAACATGAGGCTCCGTAAGAC
TTTCCTTCTCAACAGAGTGTGCCCCTCCCCCTCGCCCATGCCCGGCTGC
TCCTCTCTGCCTTAGAAGCCCTCGCCCCAGTATCCCAGGGTCTCCAAGA
TGCCCTCAGATCCATGGTCTAGAGGTATACCAGCGACCGCTGTGCCTTT
AGCCAGCTGGCAGCCTTAAGGGGAGATGAGGTCCCCCAAACGAATTCA
GTTAATGCCATCATGGGCACCACTCCCACAGCAGTTACGACCAGGGGAG
GCCAGGTGGCCCGGTGGCTCACGCCTGTAA

S 2 (SEQ ID NO: 4)

AGCCGAGATCATGCCACTGCACTCCAGCCTGGGTGACTGAGCGAGACT
GTGTCTCAAAAAAAGAAGGCATGTATCCAAATCACAAGGTTAAAAGAGA
TAAAGCATGCGAGTAAAATAAAGCAAGCCAGTCAGTGTGGGTTGCTTCT
TCCTCCCAGTGAAGGAGCTCTTTGTCAGAGGTCCTTGGATCTGTCCAAT
CTGTACCTGGAAAGGTTATTACCTGTAGGATCCTTACAGCCACACCTGG
CACACTCTGTGATCACTACCACCATCTTTGTTGCTATTATTTATGATCAT
GATTATACAATGGGTTTCTTTTCTTTCTTT

Fig. 2D

S 3 (SEQ ID NO· 5)

ttcgcggggctggggtggagctccttcctcttctccggggaccccttgtcccgtccctcccctccccttccctcccct
cccctcccctccccttcccttccctccccttcccttcccctagaaggaccagcacagcctcctacagctcccgcctg
gggtgctcctcccttgaattcagtccaggaggaagtctctgccctcttctgcccaggccaagcccctcgtcctgt
gtggacgccactccctcctggagctggtgacagctgcttacagcttagctgtcttccccaccaagtcctctgag
aaggtggcaaccagttgtgt

S 4 (SEQ ID NO: 6)

cctctctcctcttgcagCACAGAGTTGATGAGACGCGTCCGTCGCTTCCAGATTG
CTCAGTACAAGTGCCTGGTGATCAAGTATGCCAAAGACACTCGCTACAG
CAGCAGCTTCTGCACACATGACCGgtcagtccctgccccctgcagtcctgtccagtggaaa
atcacaaggcacaggacacactgttaggactctctttaatggggatggttaatcatttgaacattgaatgatt
caaatcagcacactttccaaggtgcttggcaaggtagcgcacactctccactccctgggctggagccagtggt
tctccactgaggg

Fig. 2E

S 5 (SEQ ID NO: 7)

gggaatttaaccgcacttcgtgaccatgctgtctgatgtaggtcatttacttttccaaatttgcttcctcattcct
aagatgcgatgtccacggcacagggtggtgttacacctggtggggacagggaaagcagaggaggtcacttc
gttccagctgttggaagtacaacttctggagtcagtcagatccgggattaaatatgagttctgcccgtgtgtc
acaagtcatctctaacacgggccacagaggccaaggctgggccagcagcattgatggctcgagaggctgcc
cttgcaggggccacagctggcctcccacctgcc

S 6 (SEQ ID NO: 8)

ctggccagaatacaggattttaaaaatttatgttttgcaacataattaatataaagacaaatataacccagg
cccagttctagttattcattcttctgaattttaaaaggaaacatttggctggcccctaatggtatcatgggccct
ggtacctgatgaagttggcctagtctgcccccagctcctgaacagtggaagagtttttagtctcattgagcttt
gtactggacattactaatttctaatccaaagcatcaagtgaagtggcttgtataaataactggttttcctctgg
gaggctaaggcgggtggatcacttaaaagt

Fig. 2F

S 7 (SEQ ID NO: 9)

ACCATGGAGGCACTGCCCCGCCTGCCTGCTCCGAGACGTGGCCCAGGA
GGCCCTGGGCGTGGCTGTCATAGGCATCGACGAGGGGCAGTTTgtaagttg
gcttgtcttggcatcactcttcctgccagcttccgctctgtcctcccgttttccctcgctgacttggaagttatctg
atcttttagtaaaataacaaggttaaatagctacaactagtgttggaataccctctgaaggcccctttctagtt
tccctgtcatagtgtcatagtcttgtaggattcgttttacttttttttttttttttgagacggagttttgct

S 8 (SEQ ID NO: 10)

actccagcccgggcgacaaggccagaccctgtctcaaaaaaaaaagggggaggtggggagtaatgtttgg
tttgcctcatggttccttttgcttgtttcttatacgtttattttcttgttgttgaagtaccttttttagtagtttttgca
gccaggaggtatagatgggaagctgccagtctttgtatggaaatctttcttttgtcatctagtttaagctgggc
agcaagaggtaggttgatcttgtgtgggtttgggtttttttttttttttgagacggagtcttactctgtcgcccca
ggctggagtgcaatggcgtgatct

Fig. 2G

S 9 (SEQ ID NO: 11)

tttgttagtttatcacaaagaatgaaactgaaactctctccaaggggtttagcagacttgacctcttaggtact
tttagggttgcctcgaagtacacaatgtggtggtttgatataaacataacaggaatttatttctcgctcacag
acccctacgtggttccaggccggttgatggggaggccgcccacgaggcggcttaggtcgccctggctggctg
tatacagacacggaggggaagagacgtggcggagcccctgggtgtgaggttttcatgggcctgaccagaag
ctgcaaacgtcacttctgctgatctttcaaaga

S 1 0 (SEQ ID NO: 12)

tacttgggaggctgaggcaggagaatcgcttgaacccggtaggcgaaggttgcagtgagccaagatcgccc
cattgcactccaagcctgggcaacaacaagagcaaaactcagtctcaaaacaaaacaaaacaaaagaagt
tcagggtcttcccattgcaagcagttctagatcgaggagaggggttcctagcatgggacccagcagaagga
ctgtccttcgctccttcattgtctacgtggacagtggatgaagcccagccgaacctgccttgttcccgttttctgg
gtcagcagggaaagcctttcacagagtagccaccgt

Fig. 2H

S 1 1 (SEQ ID NO: 13)

acct tgctaagccctcacgtctcaataacctcaaacctcagtacctgggctgagaaagcctgagtggccctgg
gagagagaccctgcacccaaggacaaggacatccctgcttcacccaacccaaaggccagtctggacatatg
aactcaaccagctaagagtgatatgattgattgatgagaatcaccagagcacttgccagagtttcagcttctc
cctgggccaaagtgaagtttgctttacacagtaaatgtgctctgtgcaggtcctgaatttagaaggctgtgct
gtgtcatcctgctctgtaaatggccagtaggacc

S 1 2 (SEQ ID NO· 14)

GGTGGCACCAACCTTGCTGGGACTTGGATCCCAGGGGCTTATCTCTTCA
AGTGTGGAGAGGGCAGGGTCCACGCCTCTGCTGTAGCTTATGAAATTAA
CTAATTgaaaattcactggttggtggacgcacatttctctttcacctgggtttccctgggtctcatggacag
ctccaacttgatttgggtggggattttcttccagatcttttttcttttgttttgagacagggtctctgtcgcccag
gctggagtgcagtgacgcaatccctgctcactgcagcctctgcttccccagttgaagtgattctcccccgtcagc
ct

FIG. 8

BEFORE EDITING (RED LETTERS ARE MUTANT PARTS) SEQUENCING FROM DOWNSTREAM TO UPSTREAM

GTTGGCCATGGCCTCGTAGAACTCCACGATGTCAGGGAActggaaagggcacgtggagaaagagtgtgagagcttcca (SEQ ID NO: 68)
GTTGGCCATGGCCTCGCAGAACTCCACGATGTCAGGGAActggaaagggcacgtggagaaagagtgtgagagcttcca (SEQ ID NO: 69)

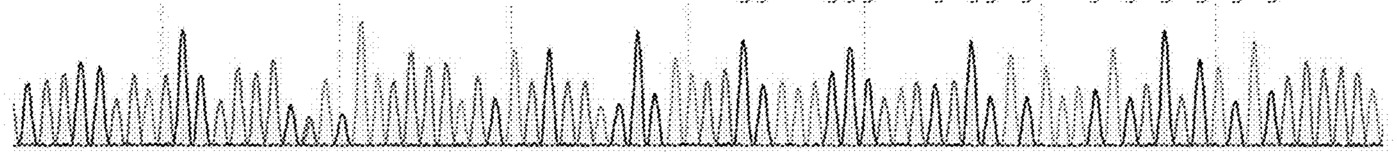

ccccagcagcagctccctggagccccagcgaagacgctgccagatcctcgagagtagggataacagggtaatggatctg (SEQ ID NO: 70)
ccccagcagcagctccctggagccccagcgaagacgctgccagatctgacaactccggccatttggcccggagtaactc (SEQ ID NO: 71)

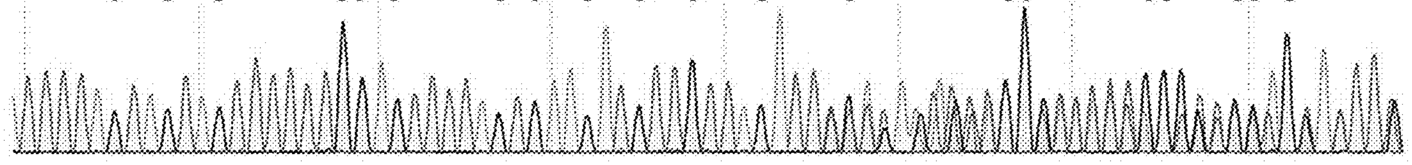

EXAMPLE WHERE BOTH ALLELES HAVE BEEN MODIFIED TO WILD TYPE

GTTGGCCATGGCCTCGCAGAACTCCACGATGTCAGGGAActggaaagggcacgtggagaaagagtgtgagagcttcca (SEQ ID NO: 72)
GTTGGCCATGGCCTCGCAGAACTCCACGATGTCAGGGAActggaaagggcacgtggagaaagagtgtgagagcttcca (SEQ ID NO: 72)

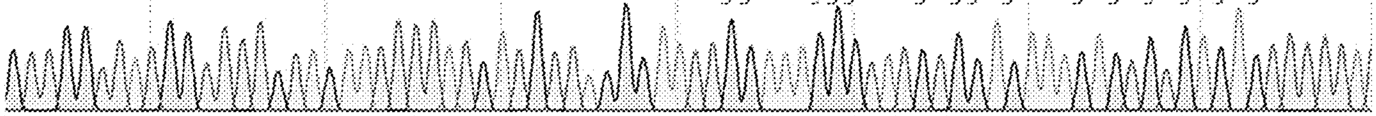

ccccagcagcagctccctggagccccagcgaagacgctgccagatctgacaactccggccatttggcccggagtaactc (SEQ ID NO: 73)
ccccagcagcagctccctggagccccagcgaagacgctgccagatctgacaactccggccatttggcccggagtaactc (SEQ ID NO: 73)

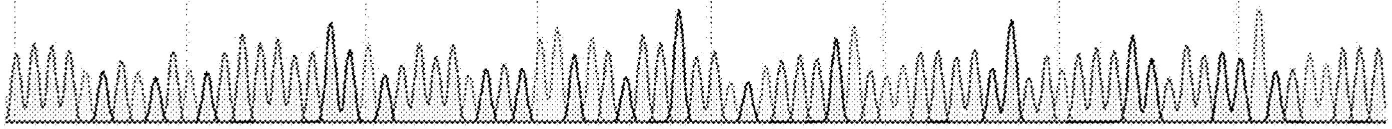

METHOD FOR PRODUCING GENOME-EDITED CELL

CROSS REFERENCE TO RELATED APPLICATIONS

This application is a National Stage of International Application No. PCT/JP2019/031117, filed Aug. 7, 2019, claiming priority to Japanese Patent Application No. 2018-215588, filed Nov. 16, 2018.

INCORPORATION BY REFERENCE OF SEQUENCE LISTING

The content of the electronically submitted sequence listing, file name: Q264044_Substitute_Sequence_Listing.txt; size: 21.1 KB; and date of creation: Aug. 28, 2024, filed herewith, is incorporated herein by reference in its entirety.

TECHNICAL FIELD

The present invention relates to a method for producing a genome-edited cell, and mainly to a method for producing a cell in which a heterozygous mutation is substituted with a normal sequence by homologous recombination between homologous chromosomes.

BACKGROUND ART

With the advent of programmable nucleases such as the TALENs and CRISPR-Cas systems, genome editing technology is now rapidly expanding. A Cas protein forms a complex with a guide RNA, and this complex binds to a target site on the genome that has a sequence complementary to the guide RNA and cleaves both of the DNA duplex. TALENs, a genome editing technique one generation ago, are a fusion protein of a TALE protein that targets DNA and a nuclease that cleaves DNA (mainly FokI), and cause a double-strand break in DNA at the target site on the genome, similar to the CRISPR-Cas systems.

When this double-strand break of DNA is repaired by non-homologous end joining, nucleotide insertion/deletion (indel) takes place, and gene knockout can be performed by frame shift or the like. Meanwhile, when donor DNA serving as a repair template is introduced from outside the cell, gene knock-in can be performed by homologous recombination between the genome and the donor DNA. In this gene knock-in, it is possible not only to insert DNA but also to cause substitution or deletion of one to several nucleotides.

However, from the viewpoint of genome homeostasis, there are serious problems in genome editing using programmable nucleases. One of them is the generation of unintended gene mutations due to double-strand breaks in DNA. In somatic cells, repair by non-homologous end joining is superior to repair by homologous recombination, and thus unintended mutations (indels) are more likely to take place at target sites that have been subjected to double-strand break by a genome editing system than knock-in with a repair template. Therefore, a cell population subjected to genome editing includes not a few cells with unintended mutations due to non-homologous end joining, in addition to the cells that have achieved the desired knock-in and the cells in which no change has taken place in the gene sequence at all. Also, at the one-cell level, even when one of the autosomal alleles is knocked in as planned, the other may have an unintended mutation. It has also been reported that programmable nucleases cause DNA double-strand breaks in DNA sequences that are highly similar to the target sequence (off-targets), resulting in genomic mutations.

In view of the above, the present inventors have developed methods that can, by using nickase-type Cas9 with one of the two nuclease sites of Cas9 inactivated, induce homologous recombination by single-strand break in DNA to suppress the occurrence of unintended mutations (indels) due to non-homologous end joining as compared with the conventional method by double-strand break in DNA. One of them is a genome editing method that utilizes a tandem nick method by using nickases to nick two sites in the target genome and one site in the donor plasmid containing the repair template (NPL 1 and PTL 1). In addition, the present inventors have further advanced this method to also develop an SNGD method that nicks one site in the target genome and nicks one site in the donor plasmid containing the repair template (a combination of single nicks in the target gene and donor plasmid) (PTL 1).

On the other hand, in genome editing, there is also a problem of random integration of donor DNA used as a repair template into the genome. That is, when a large amount of DNA is introduced into a cell, a phenomenon frequently takes place in which a part of DNA is integrated into an arbitrary part of the genome (random integration). However, it is difficult to identify the site where random integration has taken place, which poses a problem in terms of safety when performing medical applications and the like.

CITATION LIST

Patent Literature

[PTL 1] Japanese Unexamined Patent Application Publication No. 2018-11525

Non Patent Literature

[NPL 1] Nakajima K, et al., Genome Res. 28, 223-230, 2018

SUMMARY OF INVENTION

Technical Problem

The present invention has been made in view of the above-mentioned problems of the related art, and an object thereof is to provide a method for performing genome editing in a specific and highly efficient manner by homologous recombination without using exogenous donor DNA.

Solution to Problem

The present inventors have made earnest studies to achieve the above object, and as a result have conceived to avoid the problem of random integration of donor DNA by first performing genome editing using the homologous chromosome originally present in the cell as a repair template, instead of introducing donor DNA from outside the cell.

When a heterozygous mutation or complex heterozygous mutation is present on an intracellular chromosome, the gene mutation present in one allele (which is referred to as "allele A") is not present in the other allele (which is referred to as "allele B"). Here, if homologous recombination can be induced between allele A and allele B, it is possible to repair the mutation of allele A to a normal sequence using allele B as a repair template, or conversely, to introduce a mutation into the normal sequence of allele B using allele A as a template. In this case, there is no need of an exogenous donor DNA used as a template in the existing method (such as artificial synthetic DNA strand or plasmid). However, homologous recombination repair takes place between sister chromatids in somatic cells, and homologous recombination between homologous chromosomes is extremely unlikely to take place.

Therefore, the present inventors tried to induce homologous recombination between homologous chromosomes by introducing DNA cleavage around the target site of the homologous chromosomes. As a result of examining various cleavage modes, nicks were generated at multiple sites in the neighboring DNA region of the nucleotide to be modified on the recipient chromosome, and on the donor chromosome, a nick was generated at at least one site corresponding to the site where a nick was to be generated on the recipient chromosome. Thereby, the present inventors have succeeded in significantly suppressing non-homologous end joining and specifically inducing recombination between homologous chromosomes at the target site (FIGS. 1A to H show examples of introducing nicks). As a result, the present inventors have succeeded in repairing the target mutation with high efficiency without causing an unintended mutation. Moreover, the present inventors have found that, according to the principle of this method, it is possible to broadly target different bases between homologous chromosomes and unify them into any of the bases. Thus, the present invention has been completed.

The present invention relates to genome editing using homologous recombination between homologous chromosomes, and more specifically provides the following.

(1) A method for producing a genome-edited cell, comprising:

- introducing, into a cell having different bases between homologous chromosomes at a specific site of the homologous chromosomes, a combination of site-specific nickases that cleave a single strand in a neighboring DNA region of the specific site, inducing homologous recombination with one of the homologous chromosomes as a recipient and the other as a donor, and substituting the base of the recipient with the base of the donor at the specific site, wherein
- the combination of site-specific nickases causes single-strand breaks in the recipient chromosome at multiple sites in the neighboring DNA region of the specific site, and causes a single-strand break in the donor chromosome at at least one of sites corresponding to the sites of single-strand breaks in the recipient chromosome.

(2) The method according to (1), wherein the base of the recipient to be substituted is a mutant base and the base of the donor is a normal base.

(3) The method according to (1) or (2), wherein the site-specific nickases are a CRISPR-Cas system.

(4) A kit for use in the method according to any one of (1) to (3), comprising:

- a combination of site-specific nickases that cleave, in a cell having different bases between homologous chromosomes at a specific site of the homologous chromosomes, a single strand in a neighboring DNA region of the specific site, wherein
- the combination of site-specific nickases causes single-strand breaks in the recipient chromosome at multiple sites in the neighboring DNA region of the specific site, and causes a single-strand break in the donor chromosome at at least one of sites corresponding to the sites of single-strand breaks in the recipient chromosome.

Advantageous Effects of Invention

The present invention makes it possible to perform genome editing in a specific and highly efficient manner by homologous recombination between homologous chromosomes while significantly suppressing the occurrence of unintended mutations due to non-homologous end joining. In addition, since no exogenous donor DNA is used for homologous recombination and the problem of random integration of donor DNA does not occur, it is possible to perform genome editing with high safety even when medical applications such as gene therapy are performed.

BRIEF DESCRIPTION OF DRAWINGS

FIG. 2A shows the target site of crRNA designed in the present example (corresponding to the 5'-side region of sgRNA) in the thymidine kinase 1 gene of the chromosome used as the donor of homologous recombination. Uppercase letters indicate exons and lowercase letters indicate introns. The base sequences surrounded by squares are PAM sequences (hereinafter, the same applies to FIGS. 2B to H). The underlines indicate the target site of TSCER2_TK1 (ex4)-322s, and the target sites of TSCER2 TK1(ex4)21s and TSCER2 TK1(ex4)29s in order from the top.

FIG. 2B shows the target site of crRNA designed in the present example (corresponding to the 5'-side region of sgRNA) in the thymidine kinase 1 gene of the chromosome used as the recipient of homologous recombination. The underlines indicate the target site of TSCER2_TK1(ex4)-322s, the target site of TSCER2_TK1(ex4)21s, and the target sites of TSCER2 TK1(ex4)20s and TSCER2 TK1 (ex4)29s in order from the top.

FIG. 2C shows the target site of crRNA designed in the present example (corresponding to the 5'-side region of sgRNA) in the thymidine kinase 1 gene of the chromosome used as the recipient of homologous recombination. The underlines indicate the target sites of crRNAs of TSCER2_TK1(ex4)-S1 (upper part of the figure) and TSCER2_TK1(ex4)-S2 (lower part of the figure), respectively.

FIG. 2D shows the target site of crRNA designed in the present example (corresponding to the 5'-side region of sgRNA) in the thymidine kinase 1 gene of the chromosome used as the recipient of homologous recombination. The underlines indicate the target sites of crRNAs of TSCER2 TK1(ex4)-S3 (upper part of the figure) and TSCER2_TK1 (ex4)-S4 (lower part of the figure), respectively.

FIG. 2E shows the target site of crRNA designed in the present example (corresponding to the 5'-side region of sgRNA) in the thymidine kinase 1 gene of the chromosome used as the recipient of homologous recombination. The underlines indicate the target sites of crRNAs of TSCER2_TK1(ex4)-S5 (upper part of the figure) and TSCER2 TK1(ex4)-S6 (lower part of the figure), respectively.

FIG. 2F shows the target site of crRNA designed in the present example (corresponding to the 5'-side region of sgRNA) in the thymidine kinase 1 gene of the chromosome used as the recipient of homologous recombination. The underlines indicate the target sites of crRNAs of TSCER2_TK1(ex4)-S7 (upper part of the figure) and TSCER2_TK1(ex4)-S8 (lower part of the figure), respectively.

FIG. 2G shows the target site of crRNA designed in the present example (corresponding to the 5'-side region of sgRNA) in the thymidine kinase 1 gene of the chromosome used as the recipient of homologous recombination. The underlines indicate the target sites of crRNAs of TSCER2 TK1(ex4)-S9 (upper part of the figure) and TSCER2_TK1 (ex4)-S10 (lower part of the figure), respectively.

FIG. 2H shows the target site of crRNA designed in the present example (corresponding to the 5'-side region of sgRNA) in the thymidine kinase 1 gene of the chromosome used as the recipient of homologous recombination. The underlines indicate the target sites of crRNAs of TSCER2_TK1(ex4)-S11 (upper part of the figure) and TSCER2_TK1(ex4)-S12 (lower part of the figure), respectively.

FIG. 8 shows the results of analyzing the base sequence of the target site after genome editing in samples S3/20s and S12/20s of the present example shown in FIGS. 6 and 7.

DESCRIPTION OF EMBODIMENTS

Figure 1A:
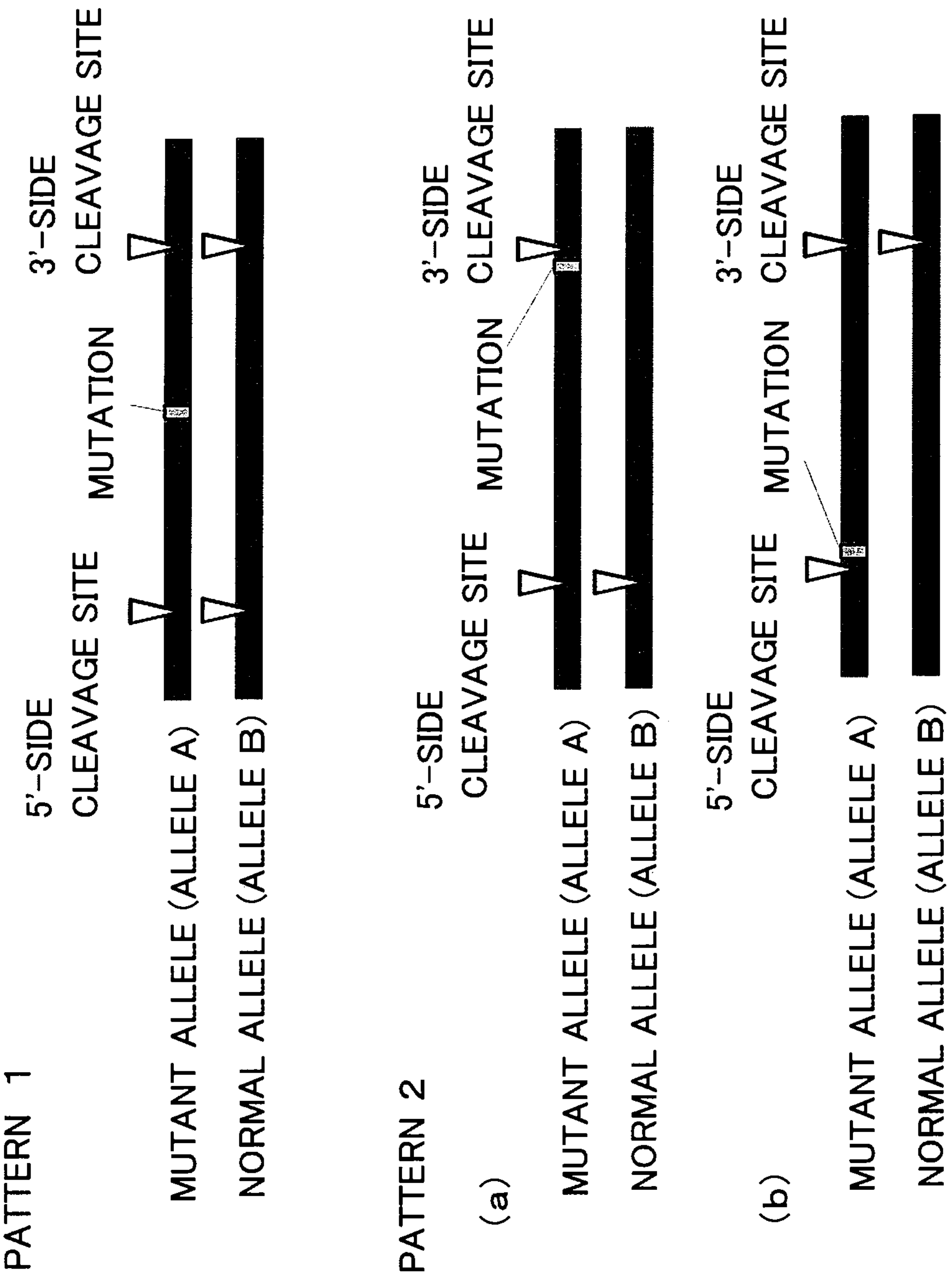
FIG. 1A shows an example of the patterns of single-strand breaks of homologous chromosomes by site-specific nickases in the method of the present invention.

The method for producing a genome-edited cell in the present invention has a principle of unifying different bases between homologous chromosomes into any of the bases by utilizing homologous recombination between homologous chromosomes induced by single-strand breaks with site-specific nickase.

Specifically, the method includes introducing, into a cell having different bases between homologous chromosomes at a specific site of the homologous chromosomes, a combination of site-specific nickases that cleave a single strand in a neighboring DNA region of the specific site, inducing homologous recombination with one of the homologous chromosomes as a recipient and the other as a donor, and substituting the base of the recipient with the base of the donor at the specific site.

The "cell" to be the target of genome editing in the present invention is not particularly limited as long as it has homologous chromosomes, and various eukaryotic cells can be targeted. Examples of "eukaryotic cells" include animal cells, plant cells, algae cells, and fungal cells. In addition to mammalian cells, examples of the animal cells include cells of fish, birds, reptiles, amphibians, and insects.

Examples of the "animal cells" include cells constituting an individual animal, cells constituting an organ-tissue extracted from an animal, cultured cells derived from an animal tissue, and the like. Specific examples include embryonic cells of embryos at various stages (such as 1-cell stage embryos, 2-cell stage embryos, 4-cell stage embryos, 8-cell stage embryos, 16-cell stage embryos, and morula stage embryos); stem cells such as induced pluripotent stem (iPS) cells, embryonic stem (ES) cells, and hematopoietic stem cells; and somatic cells such as fibroblasts, hematopoietic cells, neurons, muscle cells, osteocytes, hepatocytes, pancreatic cells, brain cells, and kidney cells. For the preparation of a genome-edited animal, a fertilized oocyte, that is, a fertilized egg, can be used. Particularly preferably, the fertilized egg is that of a pronuclear stage embryo. For the oocyte before fertilization, the cryopreserved one can be thawed and used.

In the present invention, "mammal" is a concept including human and non-human mammals. Examples of non-human mammals include even-toed undulates such as cows, wild boars, pigs, sheep, and goats, odd-toed undulates such as horses, rodents such as mice, rats, guinea pigs, hamsters, and squirrels, lagomorphs such as rabbits, and carnivores such as dogs, cats, and ferrets. The above-mentioned non-human mammal may be a domestic animal or a companion animal (pet animal), or may be a wild animal.

Examples of "plant cells" include cells of cereals, oil crops, fodder crops, fruits, and vegetables. Examples of the "plant cells" include cells constituting an individual plant, cells constituting an organ or tissue separated from a plant, cultured cells derived from a plant tissue, and the like. Examples of plant organs and tissues include leaves, stems, shoot apices (growth points), roots, tubers, root tubers, seeds, callus, and the like. Examples of plants include rice, corn, bananas, peanuts, sunflowers, tomatoes, oilseed rape, tobacco, wheat, barley, potatoes, soybeans, cotton, carnations, and the like.

The "different bases between homologous chromosomes" at a specific site of the homologous chromosomes may be one base or multiple bases (base sequence). Moreover, it may be a mutation or a polymorphism. Examples of mutations include substitutions, deletions, insertions, or combinations thereof, and examples of polymorphism include single base polymorphism and microsatellite polymorphism.

In the present invention, among homologous chromosomes, chromosomes having mutations or polymorphisms at specific sites can be used as recipients or donors in homologous recombination. Specifically, by the genome editing in the present invention, the bases at specific sites of the two chromosomes constituting the homologous chromosomes can both be made into normal sequences, or both can be made into specific mutant sequences or polymorphic sequences. For example, in HLA, the heterozygous HLA can be made into homozygous HLA.

A typical use of the present invention from the viewpoint of medical usefulness is to repair a mutation in human cells to a normal sequence in order to treat or prevent a human disease caused by heterozygous mutation. Here, the meaning of "disease caused by heterozygous mutation" includes a disease directly caused by heterozygous mutation (dominant genetic disease), as well as a disease caused by a combination of two different mutations (complex heterozygotes) (recessive genetic disease). Examples of target diseases include, but are not limited to, diseases caused by autosomal heterozygous mutations having an autosomal dominant inheritance such as OAS1 dysfunction in congenital immunodeficiency, hereditary diseases having an autosomal recessive inheritance such as ADA deficiency, and diseases that develop in X-linked sex-linked inheritance in women such as hemophilia deficient in factor VIII and factor IX in women.

The "site-specific nickase" used in the present invention is not limited as long as it can cleave a single strand of DNA in a site-specific manner on the genome, but is preferably a CRISPR-Cas system having a nickase-type Cas protein as a component. Cas proteins typically include a domain involved in cleavage of the target strand (RuvC domain) and a domain involved in cleavage of the non-target strand (HNH domain), whereas the nickase-type Cas protein typically loses its cleavage activity due to a mutation in either of these two domains. In the case of spCas9 protein (Cas9 protein derived from *S. pyogenes*), examples of such mutation include a mutation of the 10th amino acid (aspartic acid) from the N-terminus to alanine (D10A: mutation within the RuvC domain), a mutation of the 840th amino acid (histidine) from the N-terminus to alanine (H840A: mutation within the HNH domain), a mutation of the 863th amino acid (asparagine) from the N-terminus to alanine (N863A: mutation within the HNH domain), a mutation of the 762th amino acid (glutamic acid) from the N-terminus to alanine (E762A: mutation within the RuvCII domain), and a mutation of the 986th amino acid (aspartic acid) from the N-terminus to alanine (D986A: mutation within the RuvCIII domain). In addition, Cas9 proteins of various origins are known (for example, WO2014/131833), and their nickase types can be utilized. Note that amino acid sequences and base sequences of Cas9 proteins are registered in a public database, for example, GenBank (www.ncbi.nlm.nih.gov) (for example, accession number: Q99ZW2.1 and the like), and these can be used in the present invention.

Further, in the present invention, it is also possible to use Cas proteins other than Cas9, such as Cpf1 (Cas12a), Cas12b, CasX (Cas12e), and Cas14. Examples of mutations in the nickase-type Cpf1 proteins include, in AsCpf1 (Cas12), a mutation of the 1226th amino acid (arginine) from the N-terminus to alanine (R1226A: mutation within the Nuc domain). Amino acid sequences of Cpf1 are registered in a public database, for example, GenBank (www.ncbi.nlm.nih.gov) (for example, accession numbers: WP_021736722, WP_035635841, and the like).

As the protein constituting the CRISPR-Cas system, a protein added with a nuclear localization signal may be used.

In the CRISPR-Cas system including a nickase-type Cas protein as a component, the nickase-type Cas protein binds to a guide RNA to form a complex, and is targeted to a target DNA sequence to cleave a single strand of DNA. In the CRISPR-Cas9 system, the guide RNA includes crRNA and tracrRNA, but in the CRISPR-Cpf1 system, tracrRNA is unnecessary. The guide RNA in the CRISPR-Cas9 system may be a single-molecule guide RNA containing crRNA and tracrRNA, or a double-molecule guide RNA composed of a crRNA fragment and a tracrRNA fragment.

The crRNA contains a base sequence complementary to the target DNA sequence. The target DNA sequence is a base sequence composed of usually 12 to 50 bases, preferably 17 to 30 bases, and more preferably 17 to 25 bases, and is preferably selected from regions adjacent to the PAM (protospacer adjacent motif) sequence. Typically, site-specific cleavage of DNA takes place at positions determined by both the complementarity of base pairing between the crRNA and the target DNA sequence and the PAM present adjacent thereto.

In many CRISPR-Cas systems, crRNA also contains a base sequence on the 3'-side that can interact (hybridize) with the tracrRNA fragment. Meanwhile, tracrRNA contains a base sequence that can interact (hybridize) with a part of the base sequence of crRNA on the 5'-side. By the interaction of these base sequences, crRNA/tracrRNA (one molecule or two molecules) form a double-stranded RNA, and the formed double-stranded RNA interacts with the Cas protein.

PAM varies depending on the type and origin of Cas protein. Typical PAM sequences are, for example, "5'-NGG" for Cas9 protein (type II) derived from *S. pyogenes*, "5'-CCN" for Cas9 protein (type I-A1) derived from *S. solfataricus*, "5'-TCN" for Cas9 protein (type I-A2) derived from *S. solfataricus*, "5'-TTC" for Cas9 protein (type I-B) derived from *H. walsbyi*, "5'-AWG" for Cas9 protein (type I-E) derived from *E. coli*, "5'-CC" for Cas9 protein (type I-F) derived from *E. coli*, "5'-CC" for Cas9 protein (type I-F) derived from *P. aeruginosa*, "5'-NNAGAA" for Cas9 protein (type II-A) derived from S. *Thermophilus*, "5'-NGG" for Cas9 protein (type II-A) derived from *S. agalactiae*, "5'-NGRRT" or "5'-NGRRN" for Cas9 protein derived from *S. aureus*, "5'-NNNNGATT" for Cas9 protein derived from *N. meningitidis*, and "5'-NAAAAC" for Cas9 protein derived from *T. denticola*. In Cpf1, it is typically "5'-TTN" or "5'-TTTN." Note that it is also possible to modify PAM recognition by modifying the protein (for example, introducing a mutation) (Benjamin, P. et al., Nature 523, 481-485 (2015), Hirano, S. et al., Molecular Cell 61, 886-894 (2016)).

In the present invention, a site-specific nickase other than CRISPR-Cas systems can also be used. Examples of such site-specific nickase include an artificial nuclease fused with an enzyme having nickase activity. Examples of artificial nucleases usable include TALE (transcription activator-like effector), ZF (zinc finger), and PPR (pentatricopeptide repeat). Examples of enzymes capable of exerting nickase activity by fusion with these artificial nucleases include TevI (Nat Commun. 2013; 4: 1762. doi: 10.1038/ncomms2782).

These artificial nucleases are targeted to the target DNA sequence by a DNA-binding domain constructed by linking modules (peptides) that recognize specific bases (or specific base sequences), and cleave a single strand of DNA with a nickase fused to the DNA-binding domain. A suitable spacer peptide may be introduced between the DNA binding domain and the nickase in an artificial nuclease.

The present invention uses a combination of site-specific nickases that causes single-strand breaks in the recipient chromosome at multiple sites in the neighboring DNA region of the specific site (different bases between homologous chromosomes), and causes a single-strand break in the donor chromosome at at least one of sites corresponding to the sites of single-strand breaks in the recipient chromosome.

Here, the "neighboring DNA region" is a region usually within 100000 bases, 10000 bases, 5000 bases, or 2000 bases, and preferably 1000 bases (for example, within 500 bases, 400 bases, 300 bases, 200 bases, 100 bases, 50 bases, 20 bases, or 10 bases) from a specific site. Further, the "multiple sites in the neighboring DNA region" may be on the same DNA strand or on different DNA strands.

Figure 1B:
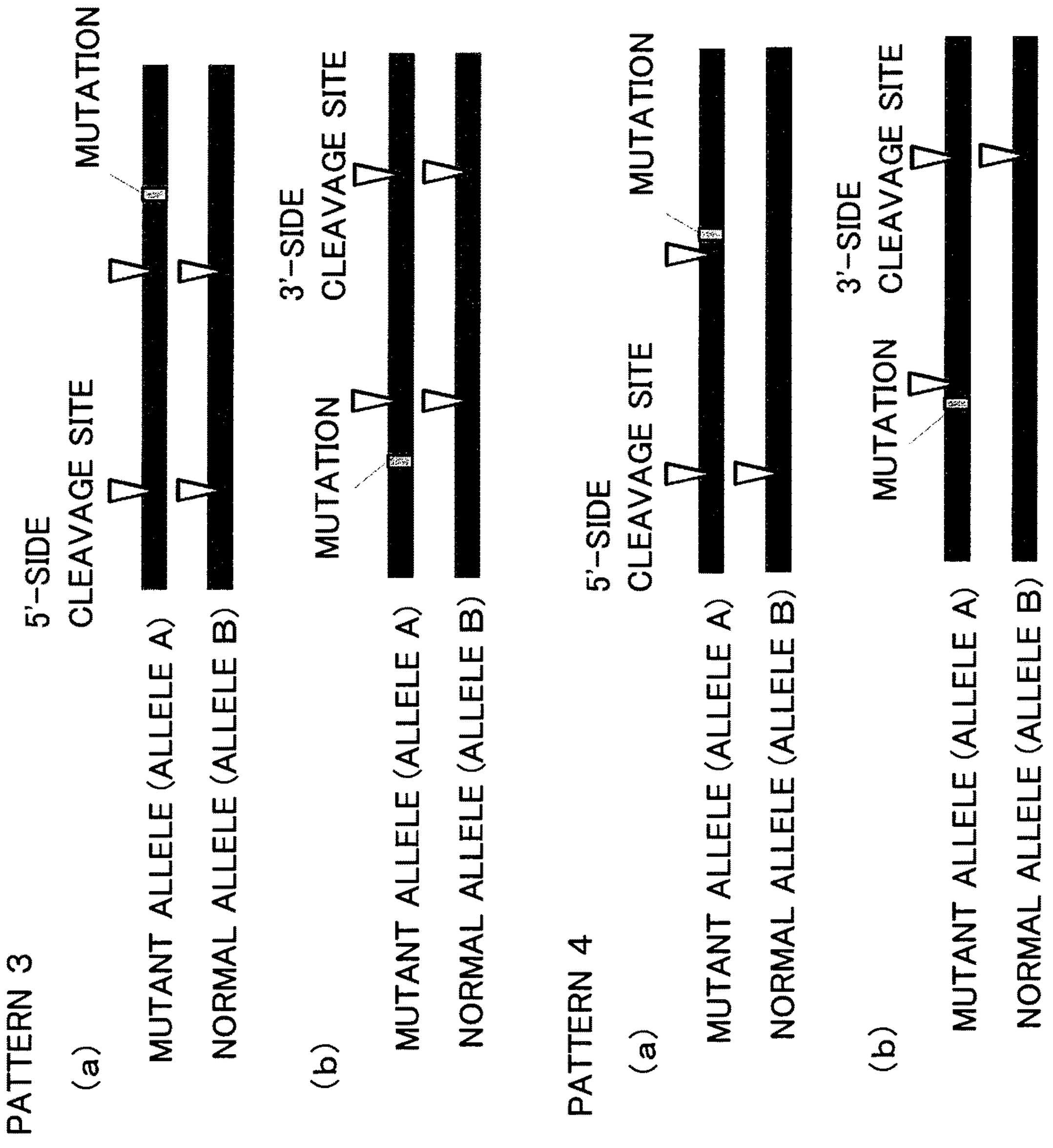
FIG. 1B is a diagram subsequent to FIG. 1A.
Figure 1C:
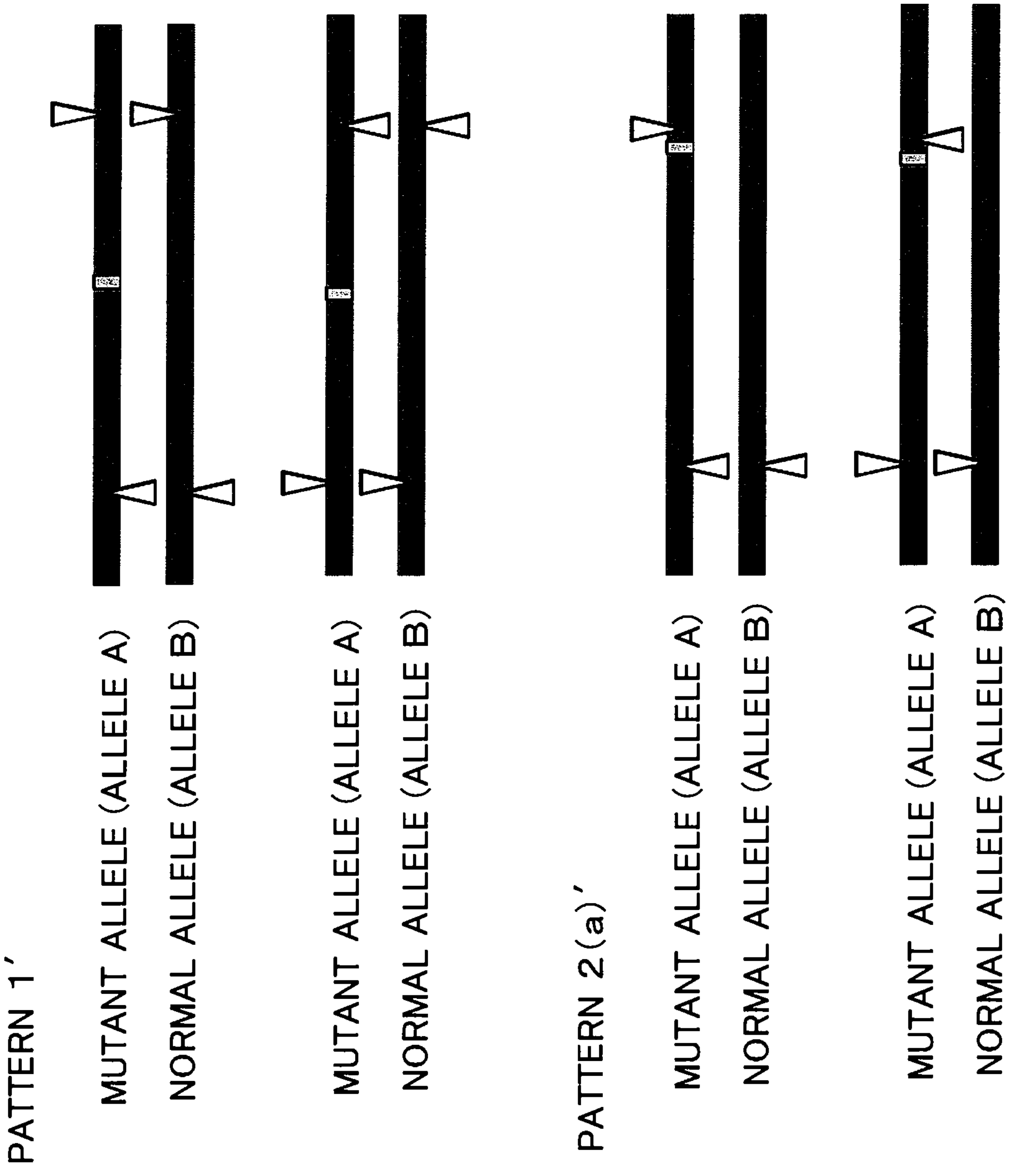
FIG. 1C is a diagram subsequent to FIG. 1B.
Figure 1D:
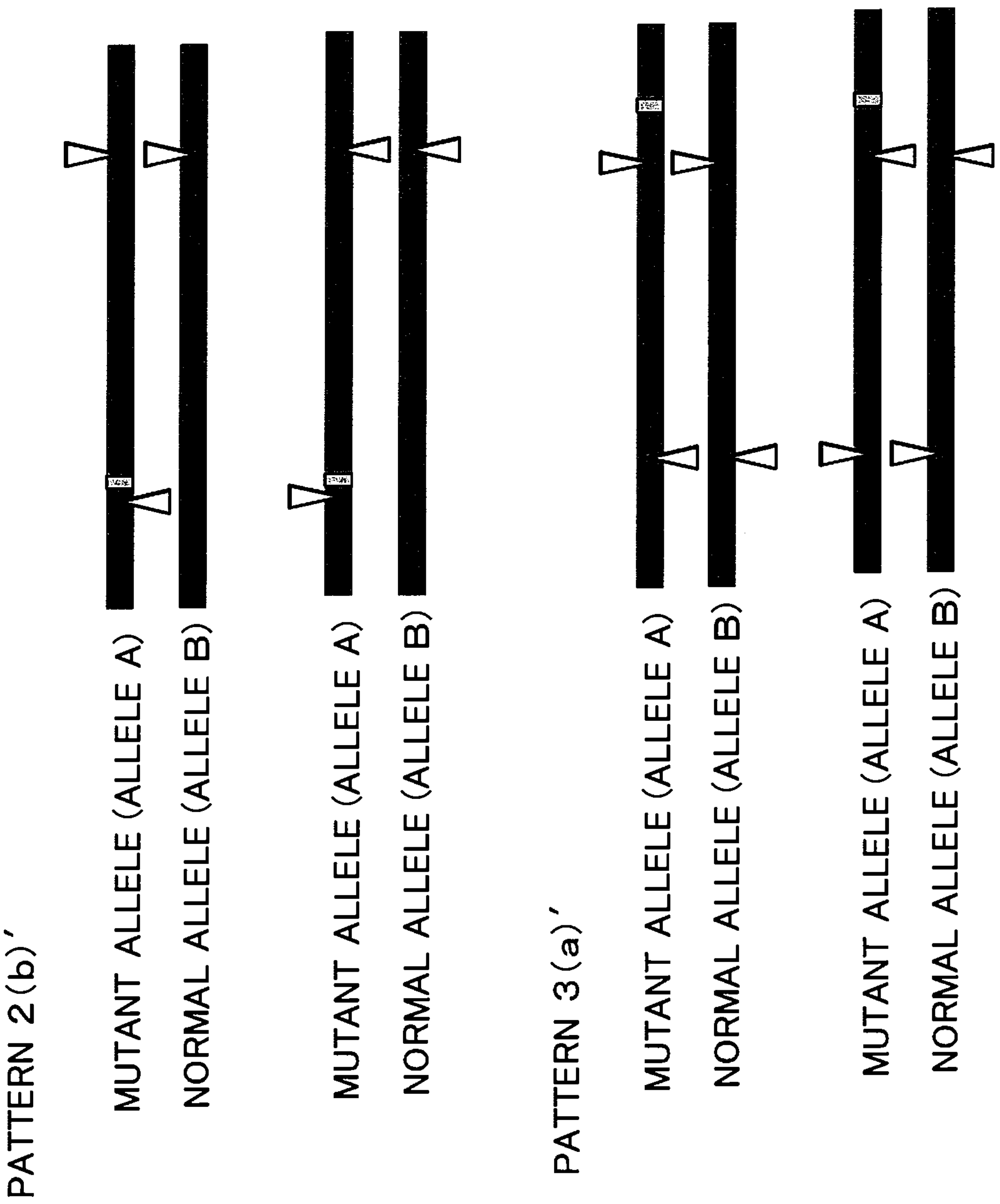
FIG. 1D is a diagram subsequent to FIG. 1C.
Figure 1E:
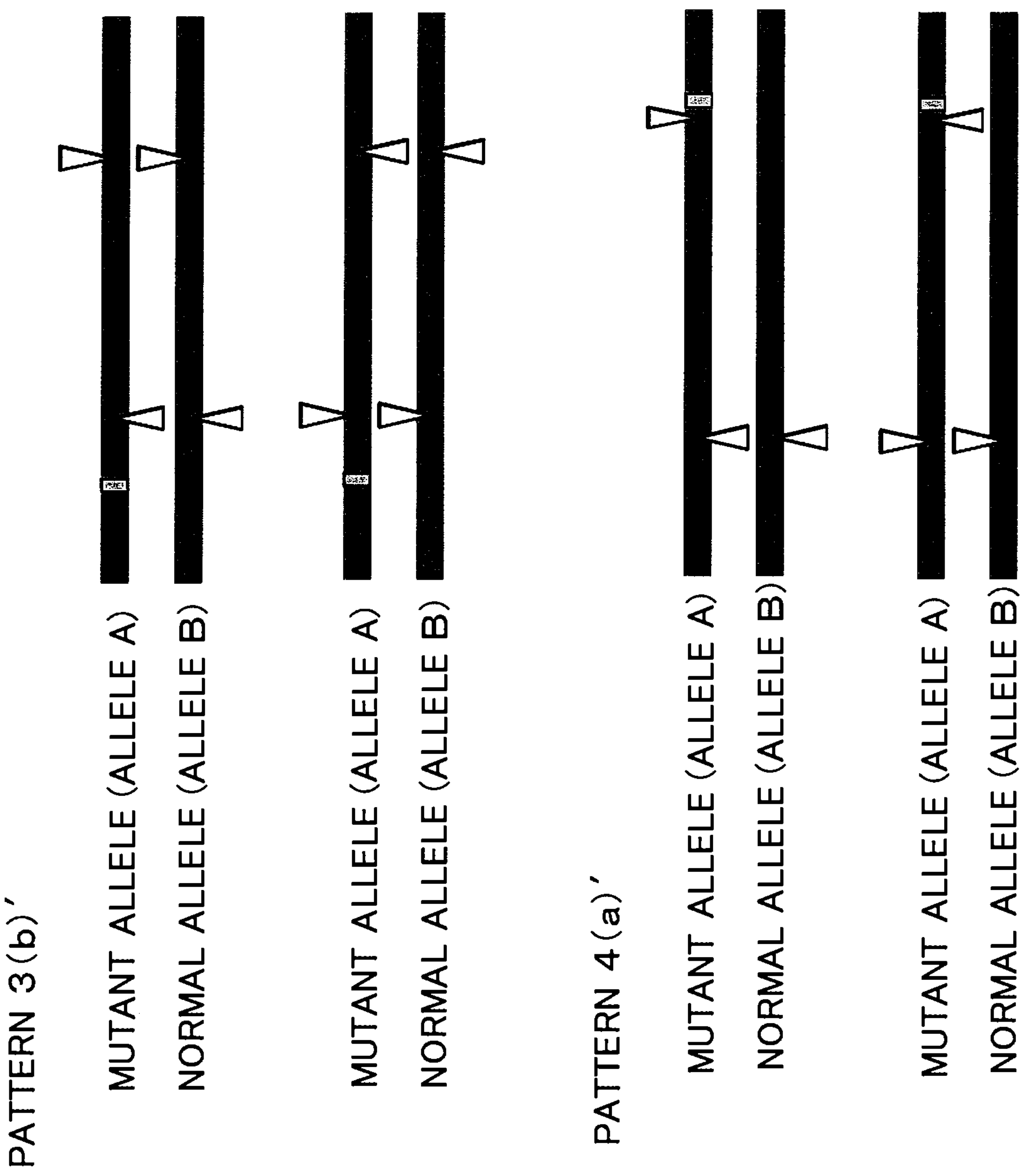
FIG. 1E is a diagram subsequent to FIG. 1D.
Figure 1F:
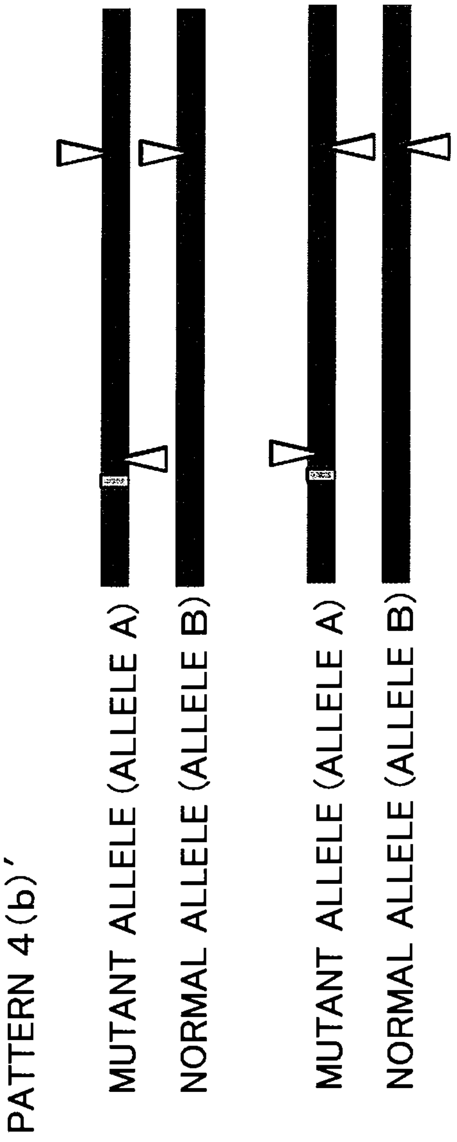
FIG. 1F is a diagram subsequent to FIG. 1E.
Figure 1G:
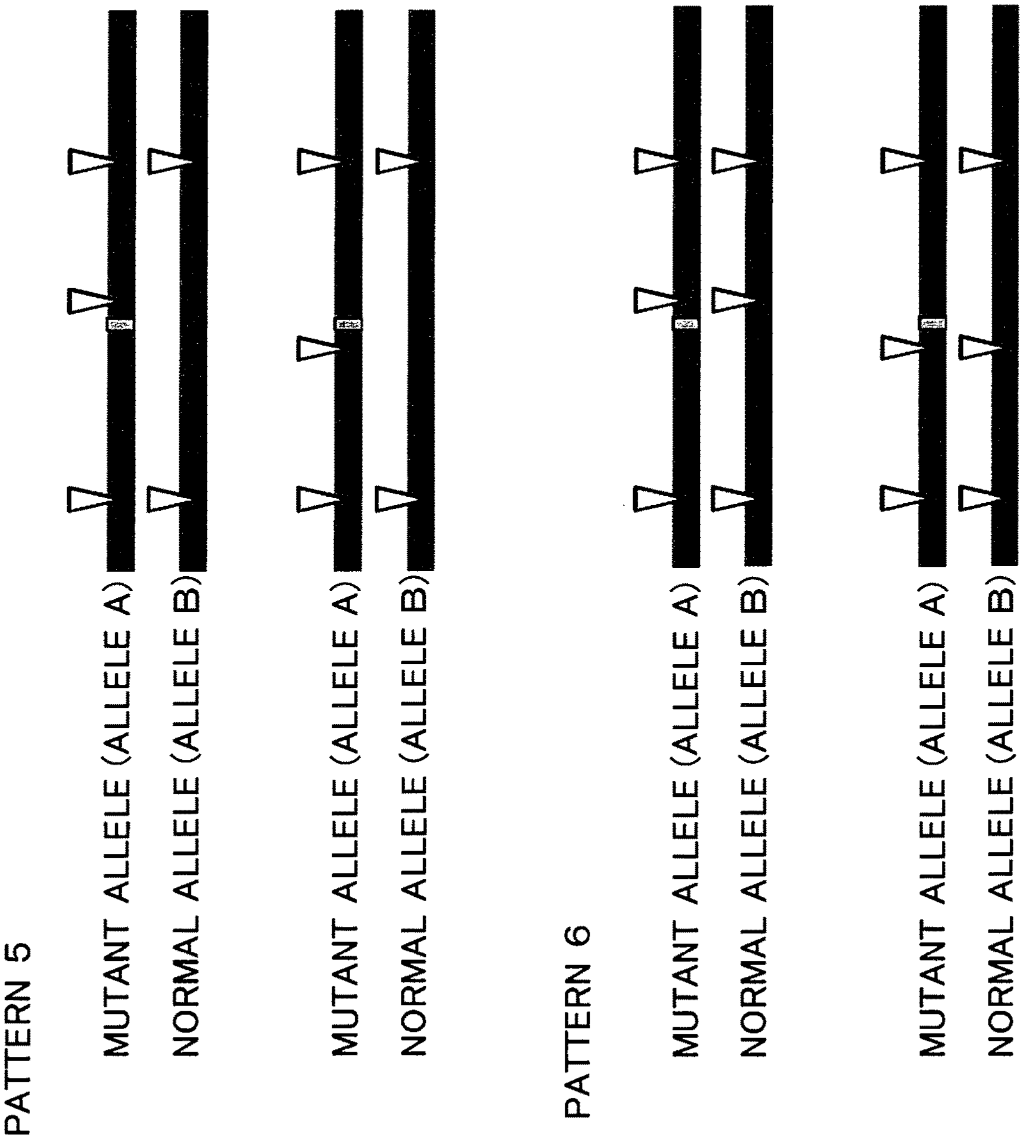
FIG. 1G is a diagram subsequent to FIG. 1F.

Specific examples of embodiment include one site each in the 5'-side-neighboring DNA region and the 3'-side-neighboring DNA region of the specific site (pattern 1 and pattern 2 in FIG. 1A, patterns 1' and 2(*a*)' in FIG. 1C, and pattern 2 (*b*)' in FIG. 1D), two sites in the 5'-side-neighboring DNA region of the specific site (pattern 3(*a*) and pattern 4(*a*) in FIG. 1B, pattern 3(*a*)' in FIG. 1D, and pattern 4(*a*)' in FIG. 1E), two sites in the 3'-side-neighboring DNA region of the specific site (pattern 3 (*b*) and pattern 4 (*b*) in FIG. 1B, pattern 3 (*b*)' in FIG. 1E, and pattern 4 (*b*)' in FIG. 1F), and at least one site each in the 5'-side-neighboring DNA region and the 3'-side-neighboring DNA region of the specific site, for a total of three sites (pattern 5 and pattern 6 in FIG. 1G). The number of sites cleaved may be four or more. In addition, in the neighboring DNA region of one specific site, other specific sites (different bases between homologous chromosomes) may be present (pattern 7 in FIG. 1H).

Figure 1H:
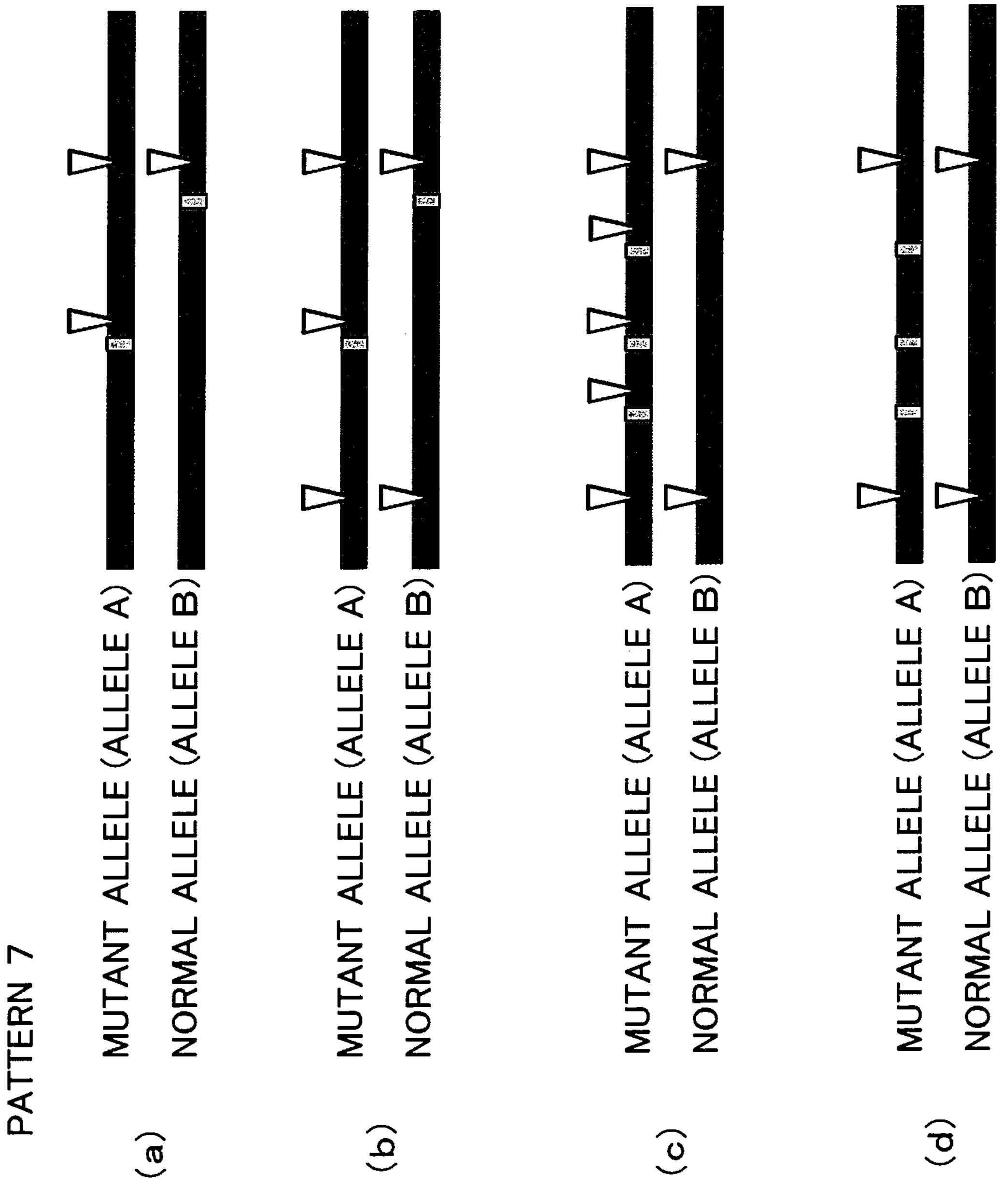
FIG. 1H is a diagram subsequent to FIG. 1G.

In an embodiment in which all the sites of single-strand breaks in the donor chromosome and the recipient chromosome correspond (pattern 1 of FIG. 1A, pattern 3 of FIG. 1B, pattern 1' of FIG. 1C, pattern 3(*a*)' of FIG. 1D, pattern 3 (*b*)' of FIG. 1E, pattern 6 of FIG. 1G, and pattern 7(*d*) of FIG. 1H), one may design such that the site-specific nickase that binds to the target DNA sequence of the recipient chromosome also binds to the corresponding DNA sequence of the donor chromosome. In this case, the target DNA sequence of the recipient chromosome and the corresponding DNA sequence of the donor chromosome are typically the same DNA sequences.

On the other hand, in an embodiment in which some of the sites of single-strand breaks in the donor chromosome and the recipient chromosome do not correspond to each other (pattern 2 in FIG. 1A, pattern 4 in FIG. 1B, pattern 2 (*a*)' in FIG. 1C, pattern 2 (*b*)' in FIG. 1D, pattern 4 (*a*)' of FIG. 1E, pattern 4 (*b*)' of FIG. 1F, pattern 5 of FIG. 1G, and patterns 7(*a*) to (*c*) of FIG. 1H), one can design such that some of the combinations of site-specific nickases that bind to the target DNA sequence of the recipient chromosome do not bind to the corresponding DNA sequence of the donor chromosome. In this case, the target DNA sequence of the recipient chromosome and the corresponding DNA sequence of the donor chromosome are different DNA sequences. For example, if the target DNA sequence of site-specific nickase is set so as to include bases to be substituted by genome editing (different bases between homologous chromosomes), the target DNA sequence of the recipient chromosome and the corresponding DNA sequence of the donor chromosome become different DNA sequences. When the site-specific nickase is a CRISPR-Cas system, one may design the guide RNA so as to have binding specificity to the target DNA sequence of the recipient. Further, in the case of an artificial nuclease in which the site-specific nickase is fused with an enzyme having nickase activity, one may design a DNA binding domain so as to have binding specificity to the target DNA sequence of the recipient. In this embodiment, due to the design of the site-specific nickase, the site of single-strand break is usually within about 100 bases, and more preferably within 50 bases (for example, within 40 bases, 30 bases, 20 bases, or 10 bases), from the specific site (different bases between homologous chromosomes).

In the present invention, when single-strand breaks are performed on different DNA strands, double-strand breaks may take place if the single-strand breaks are too close together. Therefore, the distance between single-strand breaks on different DNA strands is usually 100 bases or more, and preferably 200 bases or more, and is usually within 2000 bases, preferably within 1000 bases, and further preferably within 500 bases.

In the present invention, the combination of site-specific nickases described above is introduced into cells. In the case of a CRISPR-Cas system, the "site-specific nickases" introduced into the cells may be, for example, in the form of a combination of a guide RNA and a Cas protein, in the form of a combination of a guide RNA and a messenger RNA translated into Cas protein, or a combination of vectors expressing them, for example. The guide RNA may be modified (such as chemical modification) to suppress degradation. In the case of an artificial nuclease fused with an enzyme having nickase activity, for example, they may be in the form of a protein, a messenger RNA translated into the protein, or a vector expressing the protein.

When employing the form of an expression vector, it includes one or more regulatory elements that are operatively bound to the DNA to be expressed. Here, "operatively bound" means that the DNA is operatively bound to the regulatory elements. Examples of the "regulatory elements" include promoters, enhancers, internal ribosome entry sites (IRES), and other expression control elements (such as transcription termination signals, for example polyadenylation signals and polyU sequences). Depending on the intended purpose, the regulatory elements may, for example, direct the constitutive expression of DNA in a variety of host cells, or may direct DNA expression only in specific cells, tissues, or organs. Further, they may direct the expression of DNA only at a specific time, or may direct the expression of artificially inducible DNA. Examples of promoters include polIII promoters (such as U6 and Hi promoters), polII promoters (such as retrovirus Rous sarcoma virus (RSV) LTR promoter, cytomegalovirus (CMV) promoter, SV40 promoter, dihydrofolate reductase promoter, B-actin promoter, phosphoglycerate kinase (PGK) promoter, and EF1α promoter), polI promoters, and combinations thereof. Those skilled in the art can select an appropriate expression vector according to the type and the like of cells for introduction.

The introduction of site-specific nickases into cells can be performed by a known method such as electroporation, microinjection, DEAE-dextran method, lipofection method, nanoparticle-mediated transfection method, and virus-mediated nucleic acid delivery method.

After introduction into cells, the combination of site-specific nickases causes single-strand breaks in the recipient chromosome at multiple sites in the neighboring DNA region of the target base, and causes a single-strand break in the donor chromosome at at least one of sites corresponding to the sites of single-strand breaks in the recipient chromosome. This, while significantly suppressing the occurrence of unintended mutation due to non-homologous end joining, induces homologous recombination between homologous chromosomes and substitutes the target base with the corresponding base in the donor in a specific and highly efficient manner. According to the present invention, the occurrence of unintended mutations due to non-homologous end joining can be suppressed by 90% or more, and preferably 95% or more (for example, 96% or more, 97% or more, 98% or more, 99% or more, and 100%).

The present invention also provides a kit for use in the method of the present invention, comprising the combination of site-specific nickases. The kit may further include one or more additional reagents, and examples of the additional reagents include, but are not limited to, dilution buffers, reconstruction solutions, wash buffers, nucleic acid transfer reagents, protein transfer reagents, control reagents (such as control guide RNAs). The kit may include instructions for carrying out the method of the present invention.

EXAMPLES

Hereinafter, the present invention is described in more detail based on Examples, but the present invention is not limited to the following Examples.

[Example 1] Effectiveness of Multiple-Nick Method

A. Materials (1) TSCER2 Cells

These are cells derived from lymphoblast TK6 cells (1-nucleotide inserted into exon 4, frameshift) having a heterozygous mutation in the thymidine kinase 1 gene (TK1). Thirty-one base pairs were inserted into intron 4 of a healthy allele (which itself has nothing to do with loss of TK1 gene function) and a mutation was inserted into exon 5 to modify into a complex heterozygous mutation, resulting in loss of the functions of the TK1 gene. Since the DNA synthesis salvage pathway dependent on thymidine kinase does not function, when the DNA de novo synthesis pathway is blocked by aminopterin, cells cannot proliferate even when 2-deoxycytidine, hypoxanthine, and thymidine are supplied. When the thymidine kinase activity is restored by genome editing, cell proliferation becomes possible even in CHAR medium (10 μM 2-deoxycytidine [Sigma], 200 μM hypoxanthine [Sigma], 100 nM aminopterin [Sigma], and 17.5 μM thymidine [Sigma]).

(2) Structure of Nickase-Type CRISPR-Cas9 System and Target Region

Figure 2I:
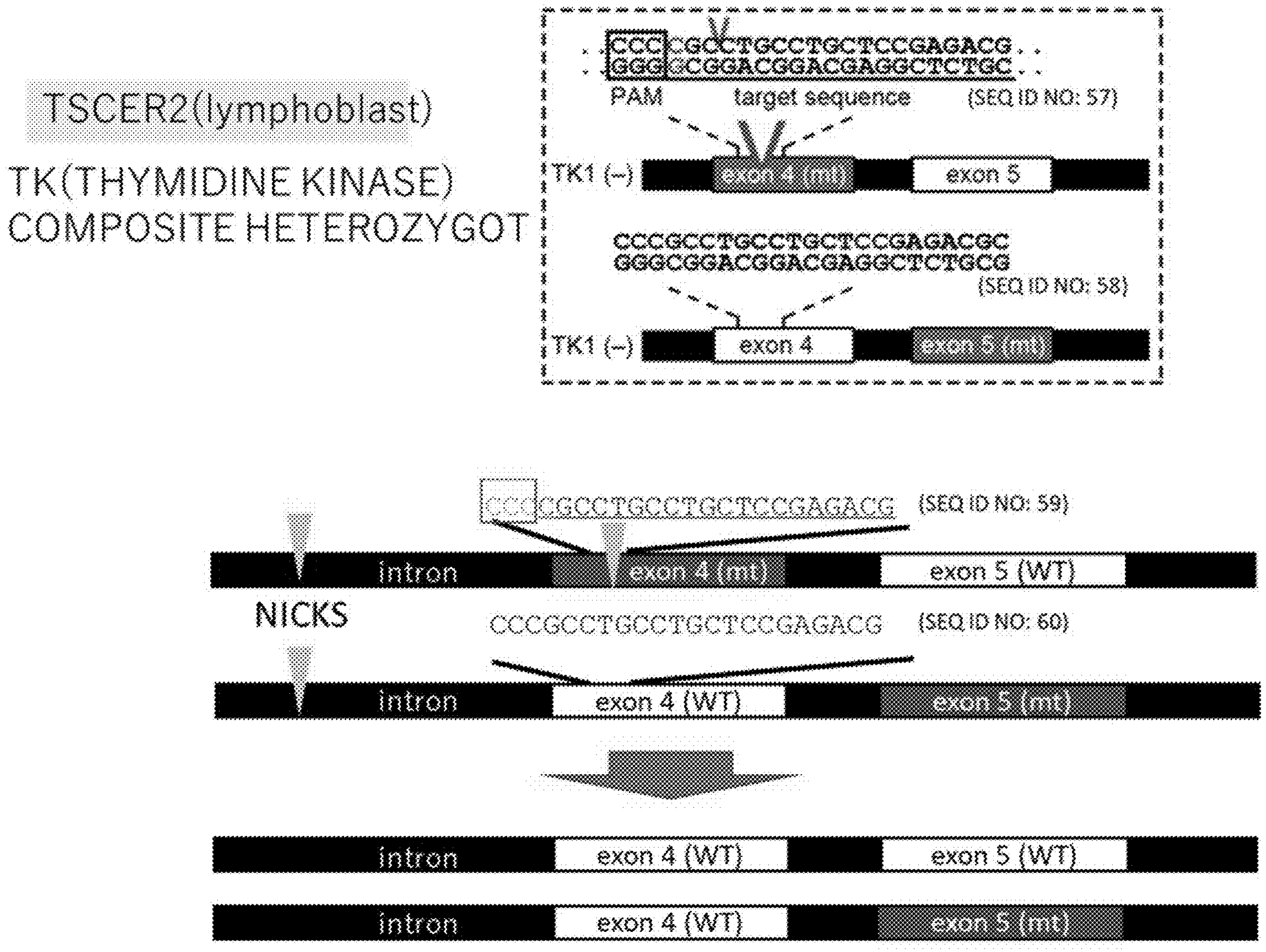
FIG. 2I shows a single-strand break at the target site when a combination of TSCER2 TK1(ex4)-322s and TSCER2_TK1(ex4)20s is used as crRNA.

The wild-type target region as a donor (the sequence of TK1 intron 3 to exon 4 to intron 4) is shown in FIG. 2A (SEQ ID NO: 1). The uppercase letters indicate exons and the lowercase letters indicate introns. The base sequences surrounded by a square are PAM sequences. The underlines indicate the target site of TSCER2_TK1(ex4)-322s, the target site of TSCER2 TK1(ex4)21s, and the target site of TSCER2_TK1(ex4)29s in order from the top.

In addition, the mutant target region as a recipient is shown in FIG. 2B (SEQ ID NO: 2). The uppercase letters indicate exons and the lowercase letters indicate introns. The base sequences surrounded by a square are PAM sequences. The underlines indicate the target site of TSCER2_TK1 (ex4)-322s, the target site of TSCER2_TK1(ex4)21s, and the target sites of TSCER2 TK1(ex4)20s and TSCER2 TK1(ex4)29s in order from the top.

The target regions of S1 to S12 are shown in FIGS. 2C to 2H (SEQ ID NOs: 3 to 14). The uppercase letters indicate exons and the lowercase letters indicate introns. The base sequences surrounded by a square are PAM sequences. The target sequence sites are underlined.

The sequence corresponding to crRNA among sgRNAs is as follows. Note that the underlines are the sequences for PAM.

```
TSCER2_TK1(ex4)20s
                                        (SEQ ID NO: 15)
CGTCTCGGAGCAGGCAGGCGGGG

TSCER2_TK1(ex4)21s
                                        (SEQ ID NO: 16)
ACGTCTCGGAGCAGGCAGGCGGG

TSCER2_TK1(ex4)-322s
                                        (SEQ ID NO: 17)
CCTCAGCCACAAGAGTAGCTGGG

TSCER2_TK1(ex4)29s
                                        (SEQ ID NO: 18)
CCTGGGCCACGTCTCGGAGCAGG

TSCER2_TK1_S1
                                        (SEQ ID NO: 19)
ACCTCTAGACCATGGATCTGAGG

TSCER2_TK1_S2
                                        (SEQ ID NO: 20)
CTGACAAAGAGCTCCTTCACTGG

TSCER2_TK1_S3
                                        (SEQ ID NO: 21)
ATTCAAGGGAGGAGCACCCCAGG

TSCER2_TK1_S4
                                        (SEQ ID NO: 22)
CTTGTGATTTTCCACTGGACAGG

TSCER2_TK1_S5
                                        (SEQ ID NO: 23)
GAAGTTGTACTTCCAACAGCTGG

TSCER2_TK1_S6
                                        (SEQ ID NO: 24)
CAGACTAGGCCAACTTCATCAGG

TSCER2_TK1_S7
                                        (SEQ ID NO: 25)
GATAACTTCCAAGTCAGCGAGGG

TSCER2_TK1_S8
                                        (SEQ ID NO: 26)
AGCTTCCCATCTATACCTCCTGG

TSCER2_TK1_S9
                                        (SEQ ID NO: 27)
CAACCGGCCTGGAACCACGTAGG

TSCER2_TK1_S10
                                        (SEQ ID NO: 28)
GATCTAGAACTGCTTGCAATGGG

TSCER2_TK1_S11
                                        (SEQ ID NO: 29)
TCAATCATATCACTCTTAGCTGG

TSCER2_TK1_S12
                                        (SEQ ID NO: 30)
GGAGCTGTCCATGAGACCCAGGG
```

A DNA double-strand break or nick is expected to take place between [CCCCGC] and [CTGCCTGCTCCGA- GACG(SEQ ID NO: 37)] in the case of using TSCER2 TK1(ex4)20s, between [CCCGCC] and [TGCCTGCTCCGAGACGT(SEQ ID NO: 38)] in the case of using TSCER2_TK1(ex4)21s, between [cccagc] and [tactcttgtggctgagg(SEQ ID NO: 39)] in the case of using TSCER2 TK1(ex4)-322s, between [CCTGCT] and [CCGAGACGTGGCCCAGG(SEQ ID NO: 40)] in the case of using TSCER2_TK1(ex4)29s, between [CCTCAG] and [ATCCATGGTCTAGAGGT(SEQ ID NO: 41)] in the case of using TSCER2_TK1_S1, between [CCAGTG] and [AAGGAGCTCTTTGTCAG(SEQ ID NO: 42)] in the case of using TSCER2_TK1_S2, between [CCTGGG] and [GTGCTCCTCCCTTGAAT(SEQ ID NO: 43)] in the case of using TSCER2_TK1_S3, between [CCTGTC] and [CAGTGGAAAATCACAAG(SEQ ID NO: 44)] in the case of using TSCER2_TK1_S4, between [CCAGCT] and [GTTGGAAGTACAACTTC(SEQ ID NO: 45)] in the case of using TSCER2_TK1_S5, between [CCTGAT] and [GAAGTTGGCCTAGTCTG(SEQ ID NO: 46)] in the case of using TSCER2_TK1_S6, between [CCCTCG] and [CTGACTTGGAAGTTATC(SEQ ID NO: 47)] in the case of using TSCER2_TK1_S7, between [CCAGGA] and [GGTATAGATGGGAAGCT(SEQ ID NO: 48)] in the case of using TSCER2_TK1_S8, between [CCTACG] and [TGGTTCCAGGCCGGTTG(SEQ ID NO: 49)] in the case of using TSCER2 TK1_S9, between [CCCATT] and [GCAAGCAGTTCTAGATC(SEQ ID NO: 50)] in the case of using TSCER2_TK1_510, between [CCAGCT] and [AAGAGTGATATGATTGA(SEQ ID NO: 51)] in the case of using TSCER2_TK1_S11, and between [CCCTGG] and [GTCTCATGGACAGCTCC(SEQ ID NO: 52)] in the case of using TSCER2_TK1_S12 (see FIGS. 2A to H and SEQ ID NOs: 1 to 14).

The [CCCCGCCTGCCTGCTCCGAGACG(SEQ ID NO: 53)] sequence on the mutant allele (the underlined is a 1-nucleotide insertion mutation) is modified by homologous interchromosomal recombination using the wild-type sequence of healthy allele as a template, and when modified as [CCCGCCTGCCTGCTCCGAGACG(SEQ ID NO: 54)], the thymidine kinase activity is restored. In addition, 1-nucleotide deletion (nucleotide deletion type) around the DNA cleavage site by Cas9 such as [CCCCGCTGCCTGCTCCGAGACG(SEQ ID NO: 55)] and [CCCCGCCGCCTGCTCCGAGACG(SEQ ID NO: 56)] also restores thymidine kinase activity (NPL 1).

Vectors expressing both Cas9 and sgRNA were used to express Cas9 and sgRNA. The vectors used are shown below.

V1: PX461(Cas9D10A-P2A-GFP)-TSCER2_TK1(ex4) 20s
V2: PX461(Cas9D10A-P2A-GFP)-TSCER2 TK1(ex4) 21s
V3: PX461(Cas9D10A-P2A-GFP)-empty
V4: PX462(Cas9D10A-P2A-PuroR)-TSCER2 TK1(ex4)-322s
V5: PX462(Cas9D10A-P2A-PuroR)-empty
V6: PX462(Cas9D10A-P2A-PuroR)-empty
V7: PX458(Cas9-P2A-GFP)-TSCER2 TK1(ex4)20s
V8: PX458(Cas9-P2A-GFP)-empty
V9: PX459(Cas9-P2A-PuroR)-empty The above vectors were combined and introduced into TSCER2 cells as follows.

Sample #1: V1+V5
Sample #2: V1+V4
Sample #3: V2+V5
Sample #4: V2+V4
Sample #5: V3+V4
Sample #6: V3+V5
Sample #7: V7+V9
Sample #8: V8+V9

Figure 3:
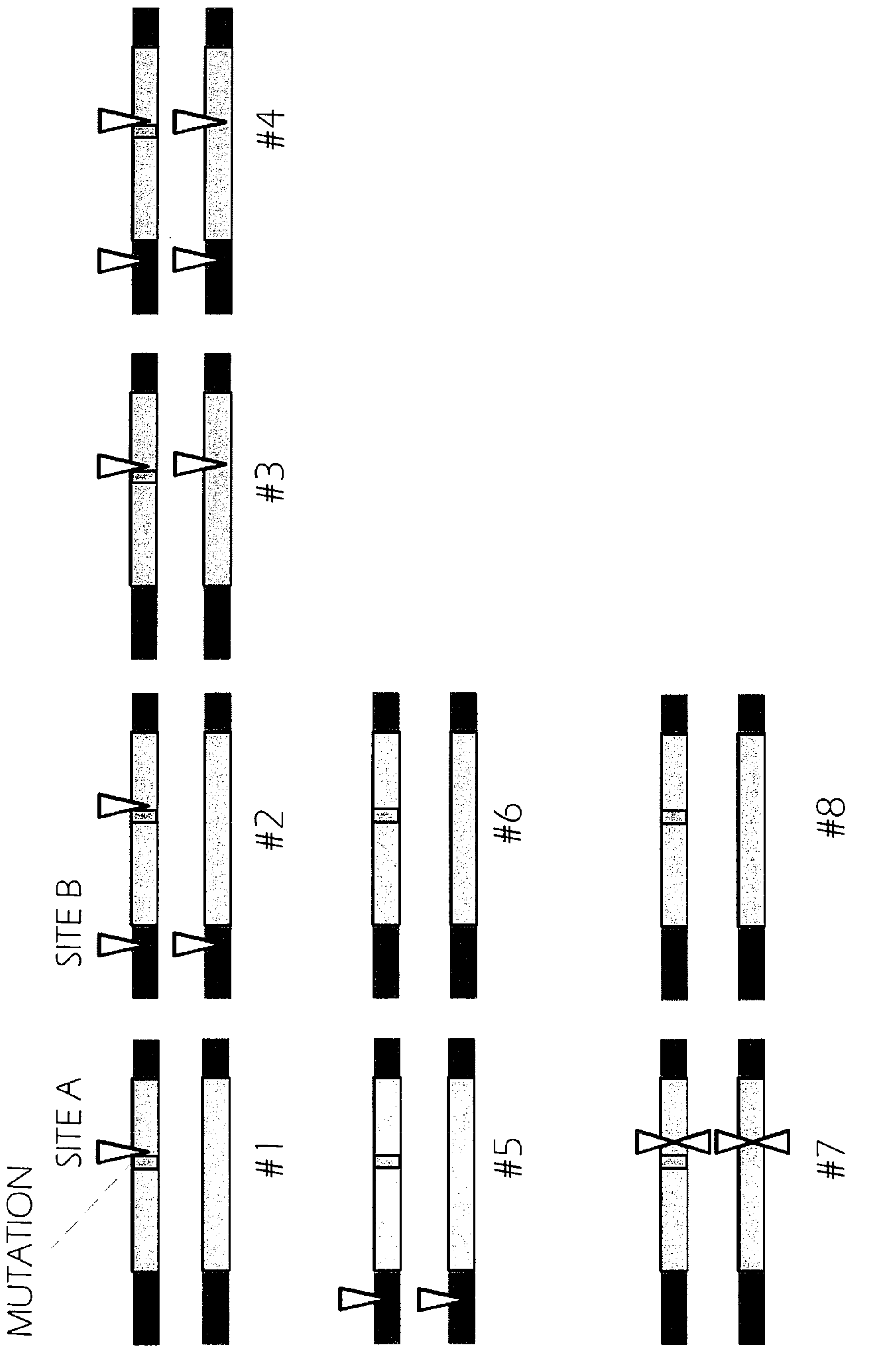
FIG. 3 shows the positions where single-strand breaks or double-strand breaks of DNA are inserted in each sample of the present example.

FIG. 3 shows the positions where nicks or DNA double-strand breaks are inserted in each sample.

B. Methods and Results

Two types of plasmids and $600\times10^4$ TSCER2 cells were mixed in 8 μg and 120 μL of R buffer (INVITROGEN™ NEON™ Transfection Kit), respectively, and 100 μL of these was electroporated by NEON™ Transfection System under the condition of 1350 V for 10 ms 3 times (electroporation condition 1). As another method, while maintaining the cell concentration and the plasmid concentration, electroporation was performed by NEON™ Transfection System under the condition of 10 μL at 1300 V for 20 ms twice (electroporation condition 2). After overnight culture at 37° C. and 5% CO2 in 10% horse serum/RPMI1640 medium, EGFP-positive cells (cells successfully transfected with PX461 or PX458 vector) were sorted using FACSARIA II™ or FACSARIA III™. The sorted cells were cultured in 10% horse serum/RPMI1640 medium for 1 day and in 5% horse serum/RPMI1640 medium for 5 days. One week after electroporation, some of the cells were transferred to CHAT medium (10 μM 2-deoxycytidine [Sigma], 200 μM hypoxanthine [Sigma], 100 nM aminopterin [Sigma], and 17.5 μM thymidine [Sigma]), dispensed into 96 plates so as to have 10, 20, 100, or 200 cells per well, and the culture was continued. In addition, for the measurement of plating efficiency, the cells in 5% horse serum-RPMI1640 medium were dispensed into 96 plates so as to have 0.5 or 1 cell per well, and cultured. After 2 weeks, the percentage of wells that had formed colonies was measured.

The percentage (%) of wells with colonies formed therein when A cells per well were sown in CHAT medium is defined as B, and the percentage (%) of wells with colonies formed therein when C cells per well were sown in normal medium is defined as D, and the editing success rate was calculated as follows.

$$(B/A)/(D/C)\times100(\%)$$

Figure 4A:
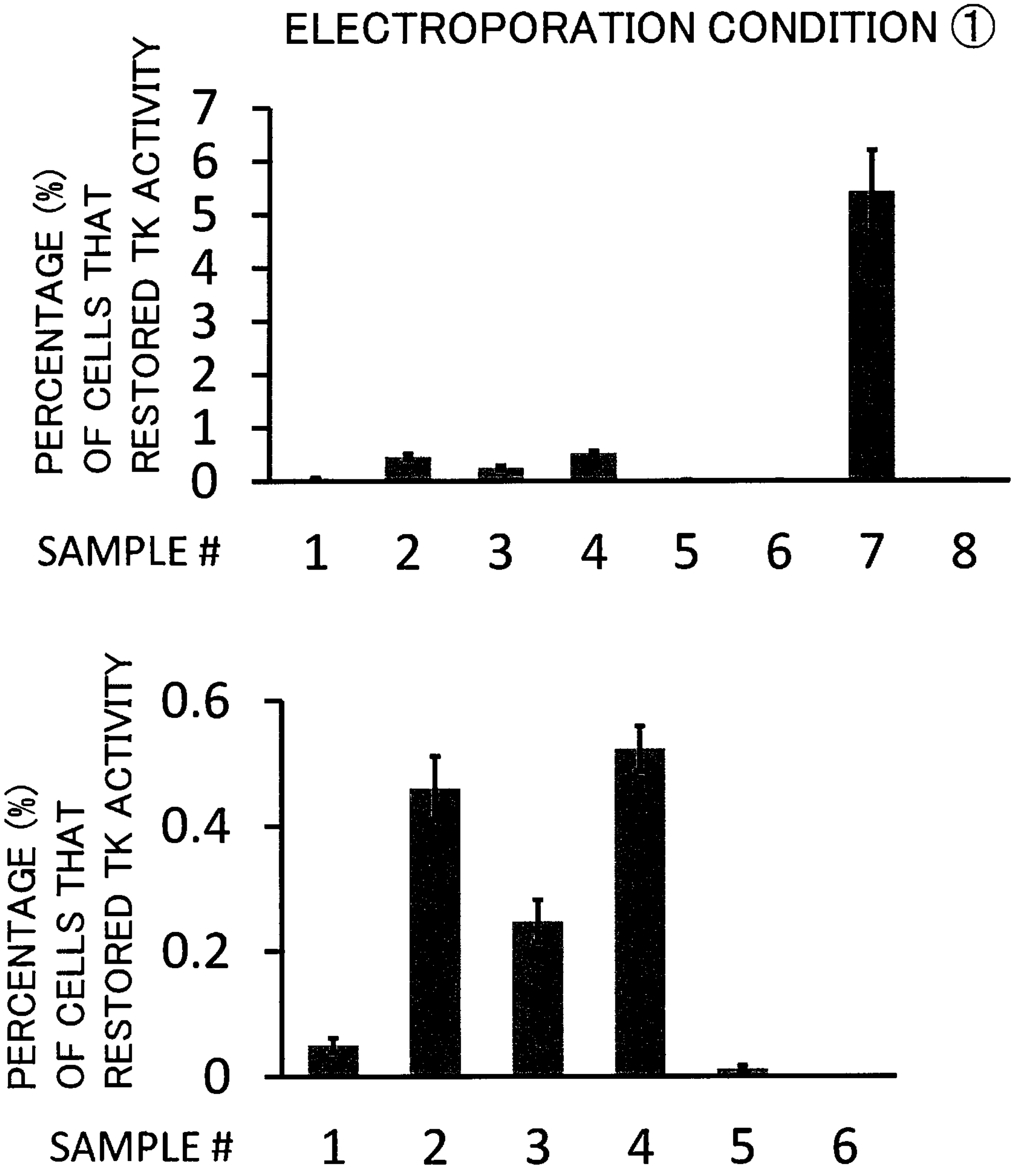
FIG. 4A shows the results of detecting cells in which genome editing took place using the recovery of thymidine kinase activity as an index in the sample of the present example shown in FIG. 3. The lower part of the figure is an enlarged graph of samples #1 to 6 on the figure.
Figure 4B:
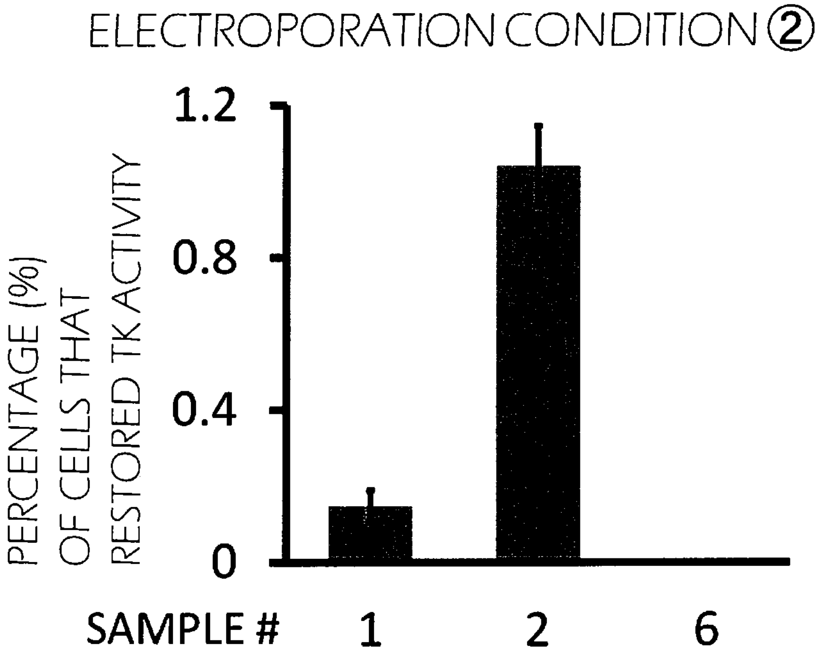
FIG. 4B shows the results of detecting cells in which genome editing took place using the recovery of thymidine kinase activity as an index in the sample of the present example shown in FIG. 3. It differs from FIG. 4A in terms of electroporation conditions when introducing a plasmid expressing the nickase-type CRISPR-Cas system into cells.

The results are shown in FIG. 4A (electroporation condition 1) and FIG. 4B (electroporation condition 2). Genome editing did not take place when the target gene was not recognized by Cas9 or Cas9 nickase (FIGS. 3, 4A, and 4B, samples #6 and #8). When DNA double-strand breaks were generated near the nucleotide to be modified, the percentage of cells that restored thymidine kinase activity reached 5.43±0.77%, and among these, those due to homologous interchromosomal recombination only reached 3.66%, where 96.3% were due to nucleotide deletions (FIGS. 3 and 4A, sample #7, and Table 1).

TABLE 1

| | #2 (Multiple-Nick Method) | #7 (Double-Strand Break Method) |
|---|---|---|
| Wild Type (Accurate) | 111/111 (100%) | 3/82 (3.66%) |
| Mutant Type | 0/111 (0%) | 79/82 (96.3%) |

Meanwhile, when nicks are generated at two sites near the nucleotide to be modified for the mutant allele (site A) and at a site distant (site B) and at one site B of the healthy allele, cellular thymidine kinase activity was restored at a percentage of 0.460±0.050% (FIGS. 3 and 4A, sample #2). When the electroporation conditions were changed, this percentage improved to 1.04±0.105% (FIG. 4B). These had higher modification efficiency than the case where one nick was inserted to the site A of the mutant allele (0.0502±0.0113%, FIGS. 3 and 4A, sample #1). For both mutant allele and healthy allele, gene modification was performed at a percentage of 0.522±0.035% even when nicks were generated at two sites, site A and site B (FIGS. 3 and 4A, sample #4).

Figure 5:
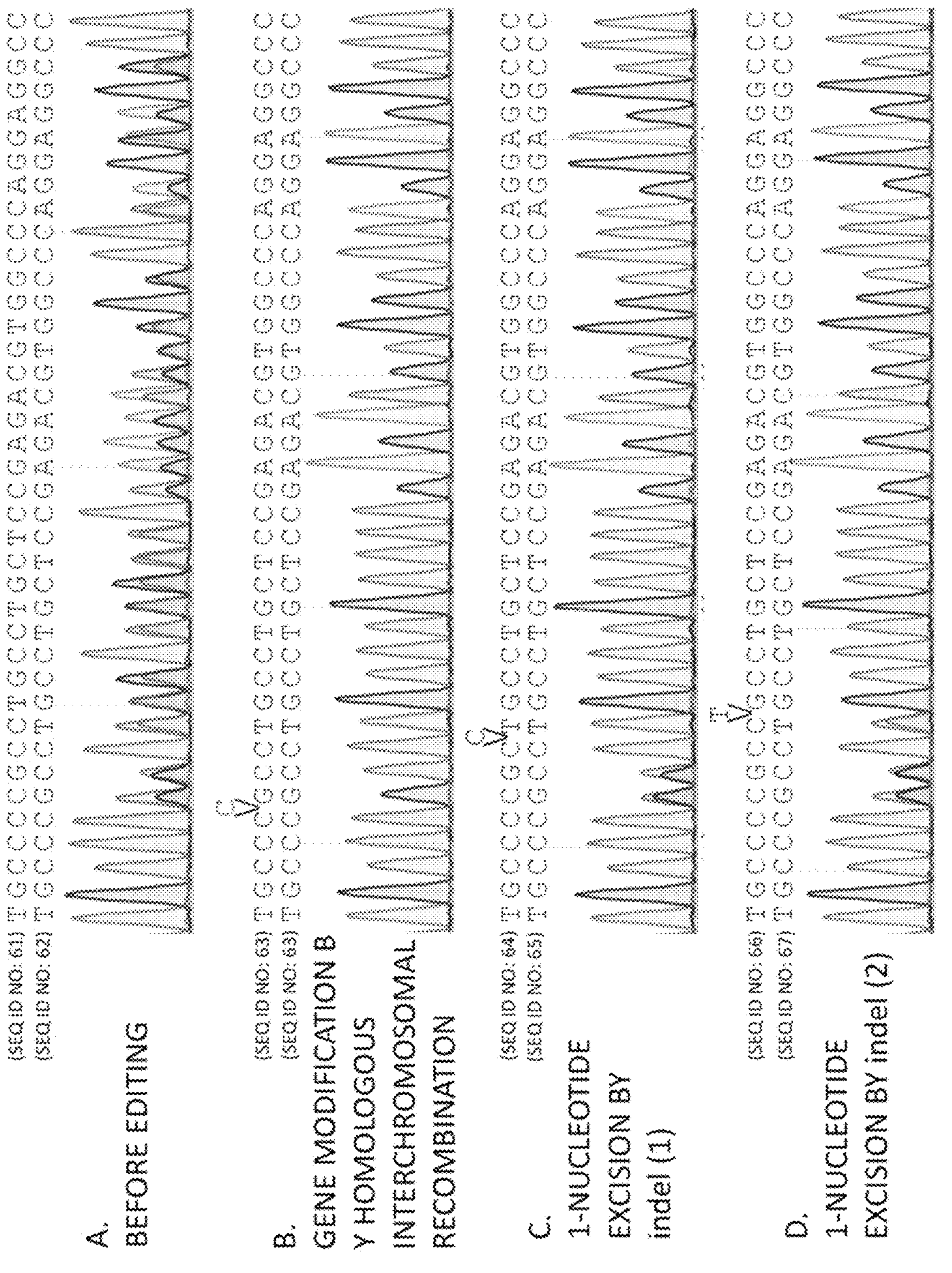
FIG. 5 shows the results of analyzing the base sequence of the target site after genome editing in samples #2 and #7 of the present example shown in FIGS. 3 and 4.

Next, in samples #2 and #7, DNA fragments in the regions intron 3 to intron 4 of the TK1 gene in the colonized cells were amplified by direct PCR. For direct PCR, MIGHTYAMP™ DNA Polymerase Ver. 2 (Takara Bio) was used. The primers used were [TCCTGAACAGTGGAAGAGTTTTTAG (SEQ ID NO: 31)] and [AACTTACAAACTGCCCCTCGTC (SEQ ID NO: 32)]. The PCR fragments were subjected to DNA sequence analysis by the Sanger sequencing method using [TGAACACTGAGCCTGCTT (SEQ ID NO: 33)] as a primer. The DNA sequence result before editing is shown in FIG. 5A, the DNA sequence result in the cell modified by homologous interchromosomal recombination is shown in FIG. 5B, and the examples of DNA sequences with nucleotide deletion are shown in FIGS. 5C and D. The percentage of cells with the mutant allele modified to wild type was 100% (111 clones/111 clones) in sample #2 (Table 1).

[Example 2] Verification of Effect of Distance Between Nicks on Genome Editing Efficiency

A. Materials

The vectors used in the present example are shown below.

VN1: PX461(Cas9D10A-P2A-GFP)-TSCER2_TK1(ex4)20s
VN2: PX462(Cas9D10A-P2A-PuroR)-TSCER2 TK1(ex4)20s
VN3: PX462(Cas9D10A-P2A-PuroR)-TSCER2_TK1(ex4)-322s
VN4: PX461(Cas9D10A-P2A-GFP)-empty
VN5: PX462(Cas9D10A-P2A-PuroR)-empty
VS1: PX462(Cas9D10A-P2A-PuroR)-TSCER2_TK1-S1
VS2: PX462(Cas9D10A-P2A-PuroR)-TSCER2_TK1-S2
VS3: PX462(Cas9D10A-P2A-PuroR)-TSCER2 TK1-S3
VS4: PX462(Cas9D10A-P2A-PuroR)-TSCER2_TK1-S4
VS5: PX462(Cas9D10A-P2A-PuroR)-TSCER2_TK1-S5
VS6: PX462(Cas9D10A-P2A-PuroR)-TSCER2 TK1-S6
VS7: PX462(Cas9D10A-P2A-PuroR)-TSCER2_TK1-S7
VS8: PX462(Cas9D10A-P2A-PuroR)-TSCER2_TK1-S8
VS9: PX462(Cas9D10A-P2A-PuroR)-TSCER2 TK1-S9
VS10: PX462(Cas9D10A-P2A-PuroR)-TSCER2_TK1-S10
VS11: PX462(Cas9D10A-P2A-PuroR)-TSCER2 TK1-S11
VS12: PX462(Cas9D10A-P2A-PuroR)-TSCER2 TK1-S12

The above vectors were combined as follows and introduced into TSCER2 cells.

−322s/20s: VN1 (1.5 μg)+VN2 (1.5 μg)+VN3 (3.0 μg)
S1/20s: VN1 (1.5 μg)+VN2 (1.5 μg)+VS1 (3.0 μg)
S2/20s: VN1 (1.5 μg)+VN2 (1.5 μg)+VS2 (3.0 μg)
S3/20s: VN1 (1.5 μg)+VN2 (1.5 μg)+VS3 (3.0 μg)
S4/20s: VN1 (1.5 μg)+VN2 (1.5 μg)+VS4 (3.0 μg)
S5/20s: VN1 (1.5 μg)+VN2 (1.5 μg)+VS5 (3.0 μg)
S6/20s: VN1 (1.5 μg)+VN2 (1.5 μg)+VS6 (3.0 μg)
S7/20s: VN1 (1.5 μg)+VN2 (1.5 μg)+VS7 (3.0 μg)
S8/20s: VN1 (1.5 μg)+VN2 (1.5 μg)+VS8 (3.0 μg)
S9/20s: VN1 (1.5 μg)+VN2 (1.5 μg)+VS9 (3.0 μg)
S10/20s: VN1 (1.5 μg)+VN2 (1.5 μg)+VS10 (3.0 μg)
S11/20s: VN1 (1.5 μg)+VN2 (1.5 μg)+VS11 (3.0 μg)
S12/20s: VN1 (1.5 μg)+VN2 (1.5 μg)+VS12 (3.0 μg)
20s/emp: VN1 (1.5 μg)+VN2 (1.5 μg)+VN5 (3.0 μg)
emp/emp: VN4 (1.5 μg)+VN5 (4.5 μg)

Figure 6:
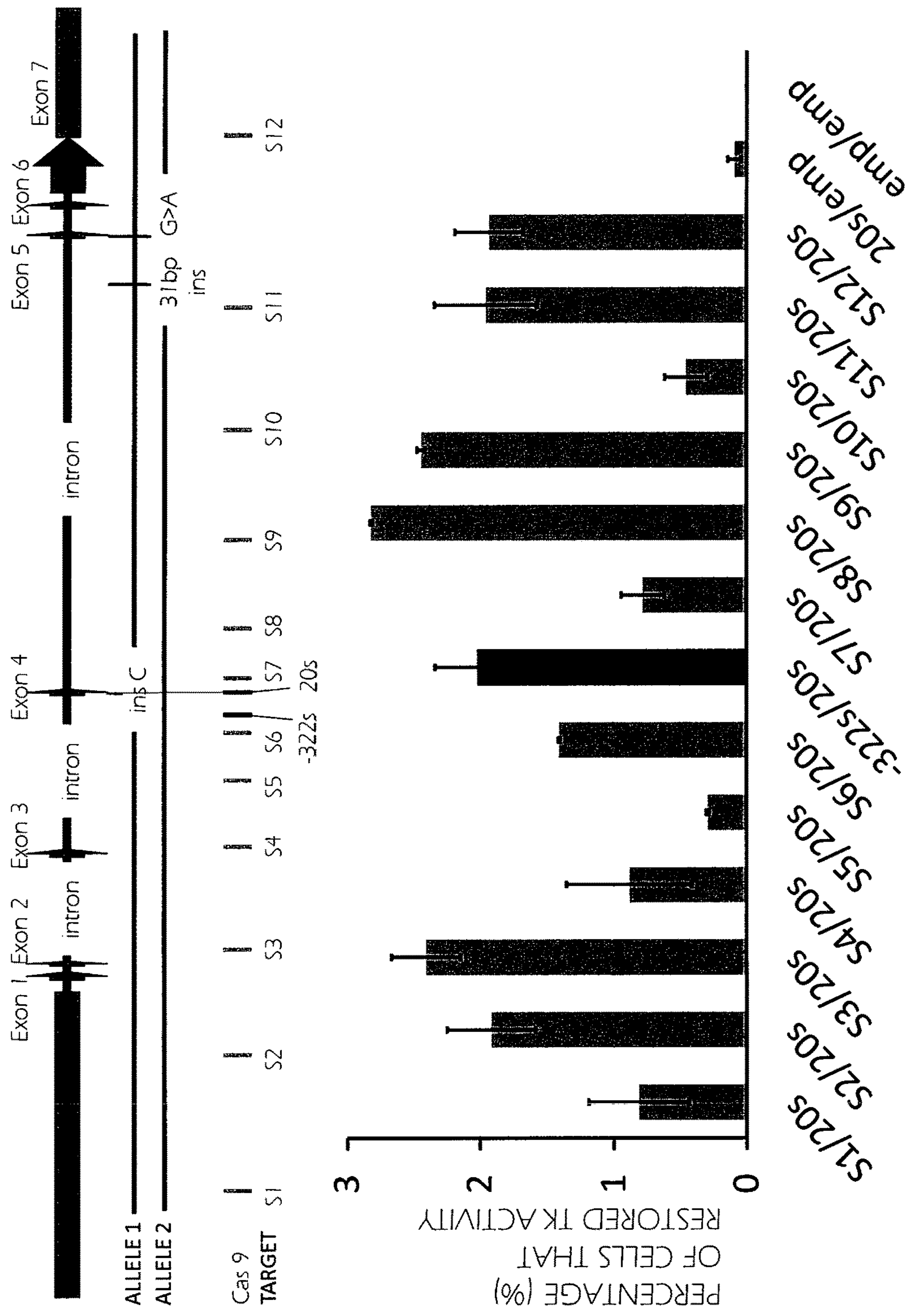
FIG. 6 shows the positions (upper part of the figure) where single-strand breaks of DNA are inserted in the samples of the present example shown in FIG. 7, and the results (lower part of the figure) of detecting cells in which genome editing took place using the recovery of thymidine kinase activity as an index.
Figure 7:
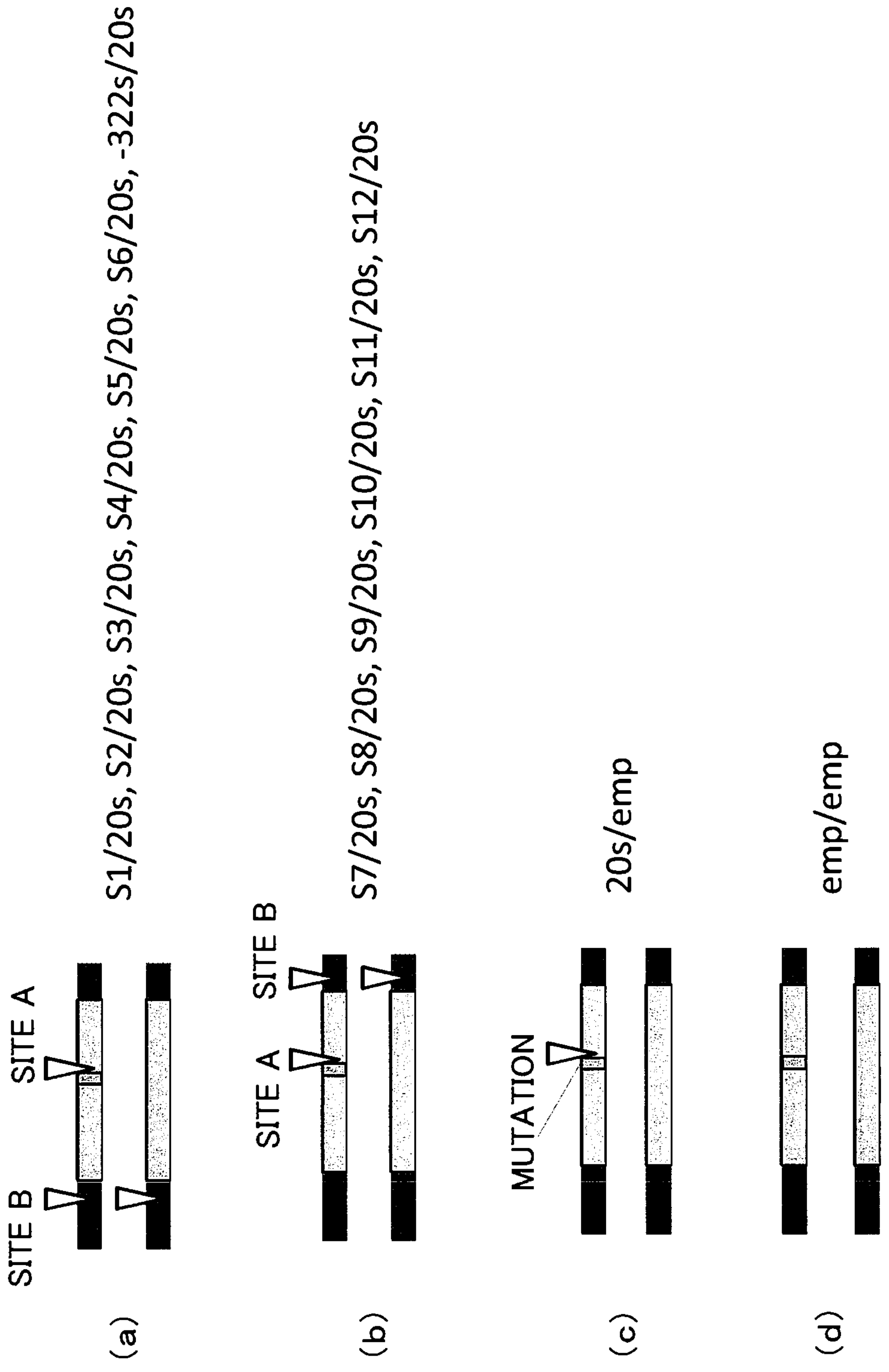
FIG. 7 shows the position where a single-strand break of DNA is inserted in each sample of the present example.

Note that the positions on the genome targeted by the guide RNA (gRNA) derived from the vectors are shown in FIG. 6. In addition, the position where a nick is inserted in each sample is shown in FIG. 7. In each sample, the expected distance between nicks (distance between site A and site B in FIG. 7) and cutting pattern (see FIGS. 1A to H) are as follows.

−322s/20s: 341 nt, pattern 2(*a*)
S1/20s: 8173 nt, pattern 2(*a*)
S2/20s: 5678 nt, pattern 2(*a*)
S3/20s: 3964 nt, pattern 2(*a*)
S4/20s: 2369 nt, pattern 2(*a*)
S5/20s: 1367 nt, pattern 2(*a*)
S6/20s: 608 nt, pattern 2(*a*)
S7/20s: 136 nt, pattern 4(*b*)
S8/20s: 1004 nt, pattern 4(*b*)
S9/20s: 2353 nt, pattern 4(*b*)
S10/20s: 4041 nt, pattern 4(*b*)
S11/20s: 6333 nt, pattern 4(*b*)
S12/20s: 8612 nt, pattern 4(*b*), pattern 7(*a*)
20s/emp.: nick at only one site
emp./emp.: no nick generated

B. Methods and Results

Each plasmid in the volume shown in the above list and $150\times10^4$ TSCER2 cells were mixed in 30 μL of R buffer (INVITROGEN™ NEON™ Transfection Kit), 10 μL of which was electroporated by NEON™ Transfection System under the condition of 1300 V for 20 ms twice (electroporation condition 2). After overnight culture at 37° C. and 5% CO2 in 10% horse serum/RPMI1640 medium, EGFP-positive cells (cells successfully transfected with PX461 vector) were sorted using FACSARIA II™ or FACSARIA III™. The sorted cells were cultured in 10% horse serum/RPMI1640 medium for 1 day and then in 5% horse serum/RPMI1640 medium. One to two week after electroporation, some of the cells were transferred to CHAT medium (10 μM 2-deoxycytidine [Sigma], 200 μM hypoxanthine [Sigma], 100 nM aminopterin [Sigma], and 17.5 μM thymidine [Sigma]), dispensed into 96 plates so as to have 40 or 100 cells per well, and the culture was continued. In addition, for the measurement of plating efficiency, the cells in 5% horse serum-RPMI1640 medium were dispensed into 96 plates so as to have 1 cell per well, and cultured. After 2 to 3 weeks, the percentage of wells that had formed colonies was measured.

The results are shown in FIG. 6. Genome editing did not take place when the target gene was not recognized by Cas9 nickase (sample emp/emp in FIGS. 6 and 7). When nicks were generated at two sites near the nucleotide to be modified for the mutant allele (site A) and at a site distant (site B) and at one site B of the healthy allele, cellular thymidine kinase activity was restored at a percentage of 0.294±0.098% to 2.82±0.010% (samples—322s/20s, S1/20s, S2/20s, S3/20s, S4/20s, S5/20s, S6/20s, S7/20s, S8/20s, S9/20s, S10/20s, S11/20s, and S12/20s in FIGS. 6 and 7), and in all the samples, the modification efficiency was higher than when the nick was generated only near the nucleotide to be modified of the mutant allele (site A)

(sample 20 s/emp in FIGS. 6 and 7: recovery of cell thymidine kinase activity at a percentage of 0.0916±0.0498%).

Next, in samples S3/20s and S12/20s, DNA fragments in the regions intron 3 to intron 4 of the TK1 gene in the colonized cells and DNA fragments in the regions intron 4 to intron 5 were amplified by direct PCR or PCR using the extracted genomic DNA as a template. For genomic DNA extraction, Kaneka Easy DNA Extraction Kit Version 2 (Kaneka) was used. For direct PCR, MIGHTYAMP™ DNA Polymerase Ver. 2 (Takara Bio) was used. KOD™ plus neo (TOYOBO) was used for PCR using genomic DNA as a template. The primers for the regions intron 3 to intron 4 used were [TCCTGAACAGTGGAAGAGTTTTTAG (SEQ ID NO: 31)] and [AACTTACAAACTGCCCCTCGTC (SEQ ID NO: 32)]. The primers for the regions intron 4 to intron 5 used were [AGTTGTGGATGTACCTGTCGTCT (SEQ ID NO: 34)] and [ATGCCCGGCTCTGTCCCTTT (SEQ ID NO: 35)]. DNA sequence analysis was performed by the Sanger sequencing method, where [TGAACACT-GAGCCTGCTT (SEQ ID NO: 33)] was the primer for the PCR fragments of the regions intron 3 to intron 4 and [TAACCCTGTGGTGGCTGA (SEQ ID NO: 36)] was the primer for the PCR fragments of the regions intron 4 to intron 5. The DNA sequencing results before editing of the regions intron 4 to intron 5 are shown in the upper panel of FIG. 8, and the DNA sequencing results in the cells in which both alleles became wild type by homologous interchromosomal recombination are shown in the lower panel of FIG. 8.

In both of the samples S3/20s and S12/20s, no new mutation was observed in exon 4 and exon 5 due to genome editing. In sample S3/20s, 98.9% was modified in exon 4 and 1.06% was modified in exon 5. There were no cells in which both exon 4 and exon 5 had been modified. In sample S12/20s, 83.2% was modified in exon 4 and 30.5% in exon 5. The cells in which both exon 4 and exon 5 were modified were 13.7% (Table 2). In all of the cells in which exon 5 was modified, the 31-nucleotide insertion mutation present in intron 4 was also modified.

TABLE 2

| | Exon 4 Modified Exon 5 Unmodified | Exon 4 Unmodified Exon 5 Modified | Exon 4 Modified Exon 5 Modified | Other |
|---|---|---|---|---|
| S3/20s | 93/94 (98.9%) | 1/94 (1.06%) | 0/0 (0.0%) | 0/0 (0.0%) |
| S12/20s | 66/95 (69.5%) | 16/95 (16.8%) | 13/95 (13.7%) | 0/0 (0.0%) |

With a pattern such as S12/20s (pattern 7 (*a*)), it was possible to simultaneously modify 3 mutations, 1-nucleotide insertion of exon 4, 31-nucleotide insertion of intron 4, and 1-base substitution of exon 5. [Example 3] Verification of Effect of Introducing Additional Single-Strand Breaks on Genome Editing Efficiency A. Materials The vectors used in the present example are shown below. In the present example, the vectors were combined and introduced into TSCER2 cells as follows.

S3/20s/S8: VN1 (1.5 μg)+VN2 (1.5 μg)+VS3 (3.0 μg)+VS8 (3.0 μg)

S3/20s/S11: VN1 (1.5 μg)+VN2 (1.5 μg)+VS3 (3.0 μg)+VS11 (3.0 μg)

S6/20s/S8: VN1 (1.5 μg)+VN2 (1.5 μg)+VS6 (3.0 μg)+VS8 (3.0 μg)

S6/20s/S11: VN1 (1.5 μg)+VN2 (1.5 μg)+VS6 (3.0 μg)+VS11 (3.0 μg)

S3/20s/emp: VN1 (1.5 μg)+VN2 (1.5 μg)+VS3 (3.0 μg)+VN5 (3.0 μg)

S6/20s/emp: VN1 (1.5 μg)+VN2 (1.5 μg)+VS6 (3.0 μg)+VN5 (3.0 μg)

20s/S8/emp: VN1 (1.5 μg)+VN2 (1.5 μg)+VS8 (3.0 μg)+VN5 (3.0 μg)

20s/S11/emp: VN1 (1.5 μg)+VN2 (1.5 μg)+VS11 (3.0 μg)+VN5 (3.0 μg)

20s/emp/emp: VN1 (1.5 μg)+VN2 (1.5 μg)+VN5 (6.0 μg)

emp/emp/emp: VN4 (1.5 μg)+VN5 (7.5 μg)

Figure 9:
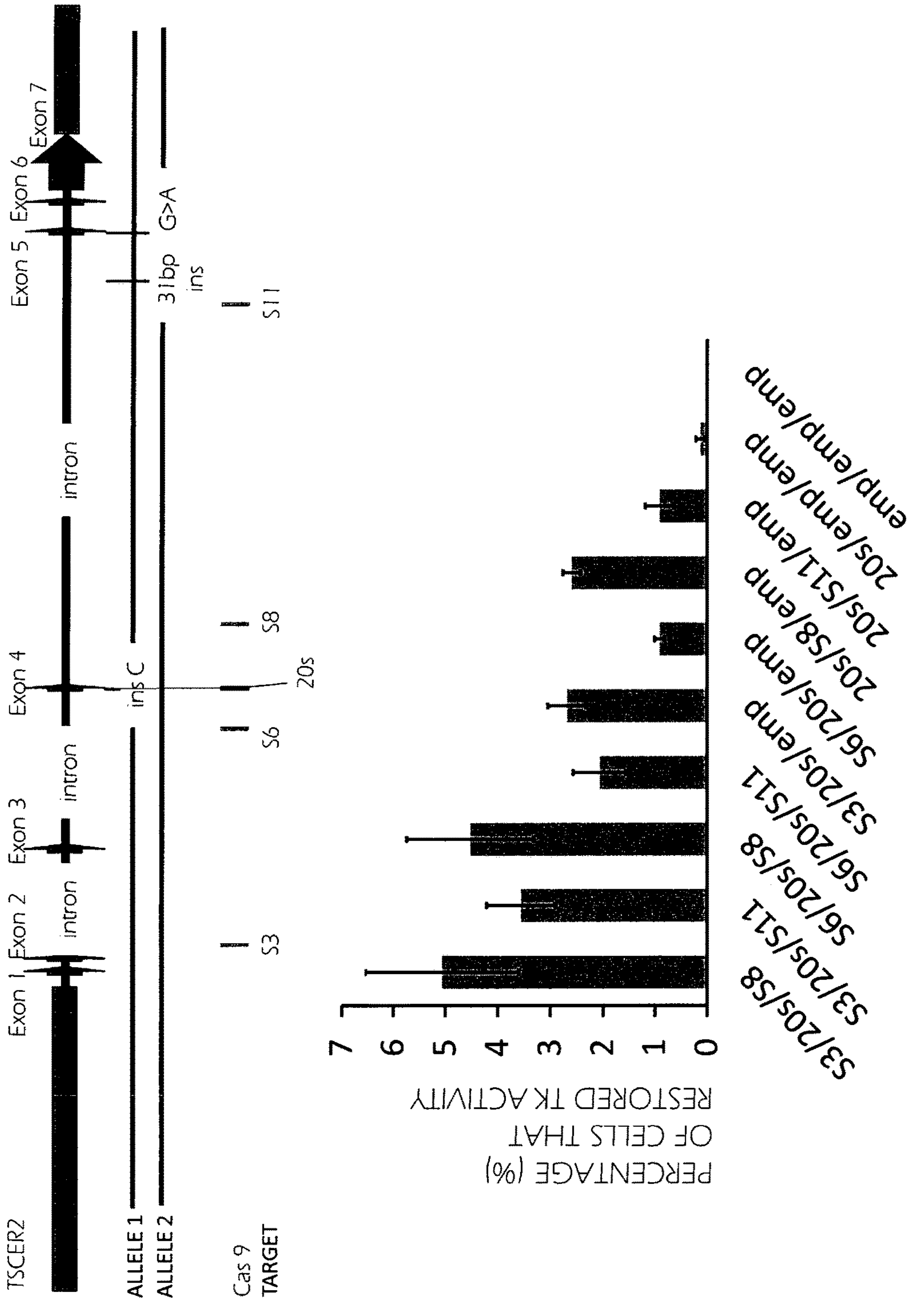
FIG. 9 shows the positions (upper part of the figure) where single-strand breaks of DNA are inserted in each sample of the present example shown in FIG. 10, and the results (lower part of the figure) of detecting cells in which genome editing took place using the recovery of thymidine kinase activity as an index.
Figure 10:
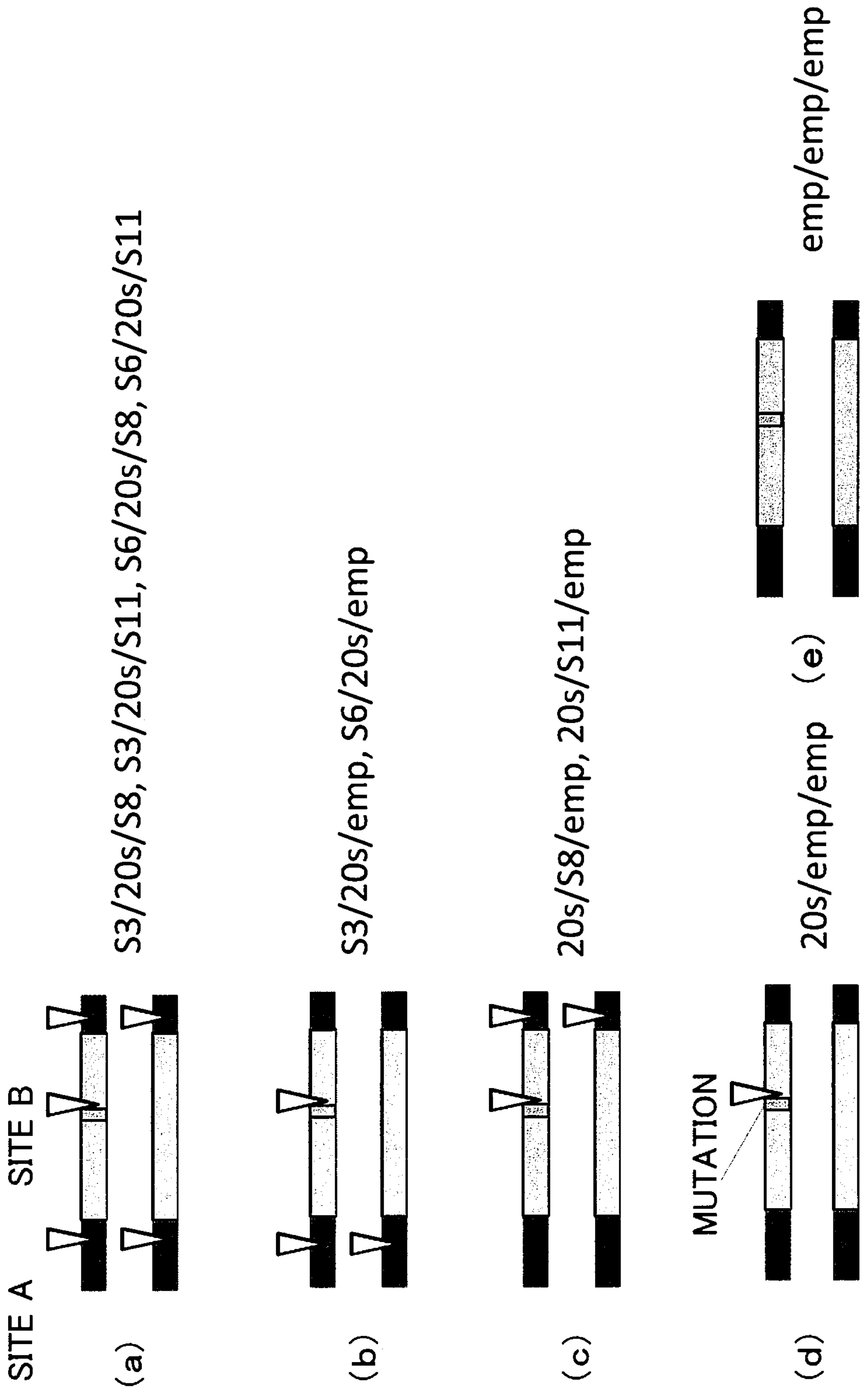
FIG. 10 shows the position where a single-strand break of DNA is inserted in each sample of the present example.

Note that the positions on the genome targeted by the guide RNA (gRNA) derived from the vectors are shown in FIG. 9. In addition, the position where a nick is inserted in each sample is shown in FIG. 10. In each sample, the cutting pattern (see FIGS. 1A to H) is as follows.

S3/20s/S8: pattern 5

S3/20s/S11: pattern 5

S6/20s/S8: pattern 5

S6/20s/S11: pattern 5

S3/20s/emp: pattern 2(*a*)

S6/20s/emp: pattern 2(*a*)

20s/S8/emp: pattern 4(*b*)

20s/S11/emp: pattern 4(*b*)

20s/emp/emp: nick at only one site emp/emp/emp: no nick generated

B. Methods and Results

Each plasmid in the volume shown in the above list and $150 \times 10^4$ TSCER2 cells were mixed in 30 μL of R buffer (INVITROGEN™ NEON™ Transfection Kit), 10 μL of which was electroporated by NEON™ Transfection System under the condition of 1300 V for 20 ms twice (electroporation condition 2). After overnight culture at 37° C. and 5% CO2 in 10% horse serum/RPMI1640 medium, EGFP-positive cells (cells successfully transfected with PX461 vector) were sorted using FACSARIA II™ or FACSARIA III™. The sorted cells were cultured in 10% horse serum/RPMI1640 medium for 1 day and then in 5% horse serum/RPMI1640 medium for 5 days. One to two week after electroporation, some of the cells were transferred to CHAT medium (10 μM 2-deoxycytidine [Sigma], 200 μM hypoxanthine [Sigma], 100 nM aminopterin [Sigma], and 17.5 μM thymidine [Sigma]), dispensed into 96 plates so as to have 20 or 200 cells per well, and the culture was continued. In addition, for the measurement of plating efficiency, the cells in 5% horse serum-RPMI1640 medium were dispensed into 96 plates so as to have 1 cell per well, and cultured. After 2 to 3 weeks, the percentage of wells that had formed colonies was measured.

The results are shown in FIG. 9. Compared with sample S3/20s/emp (2.68±0.37%) and sample 20s/S8/emp (2.59±0.17%), which have nicks at two sites in the recipient allele and at one site in the donor allele, the percentage of cells that restored the thymidine kinase activity was as highly efficient as 5.07±1.47% in sample S3/20s/S8, which has nicks at three sites in the recipient allele and at two sites in the donor allele. It was shown that the percentage of cells that restored thymidine kinase activity in sample S3/20s/S11 was also higher than in sample S3/20s/emp and sample 20s/S11/emp, the percentage of cells that restored thymidine kinase activity in sample S6/20s/S8 was also higher than in sample S6/20s/emp and sample 20s/S8/emp, and the percentage of cells that restored thymidine kinase activity in sample S6/20s/S11 was also higher than in sample S6/20s/emp and sample 20s/S11/emp. [Example 4] Verification of Genome Editing Efficiency by Multiple-Nick Method without Using Foreign DNA A. Materials An sgRNA targeting the regions (S3, 20s, 29s, S8) shown in FIG. 11 or an sgRNA (no) having no target sequence in the human genome was combined as follows and introduced into TSCER2 cells together with Cas9D10A mRNA.

Figure 12:
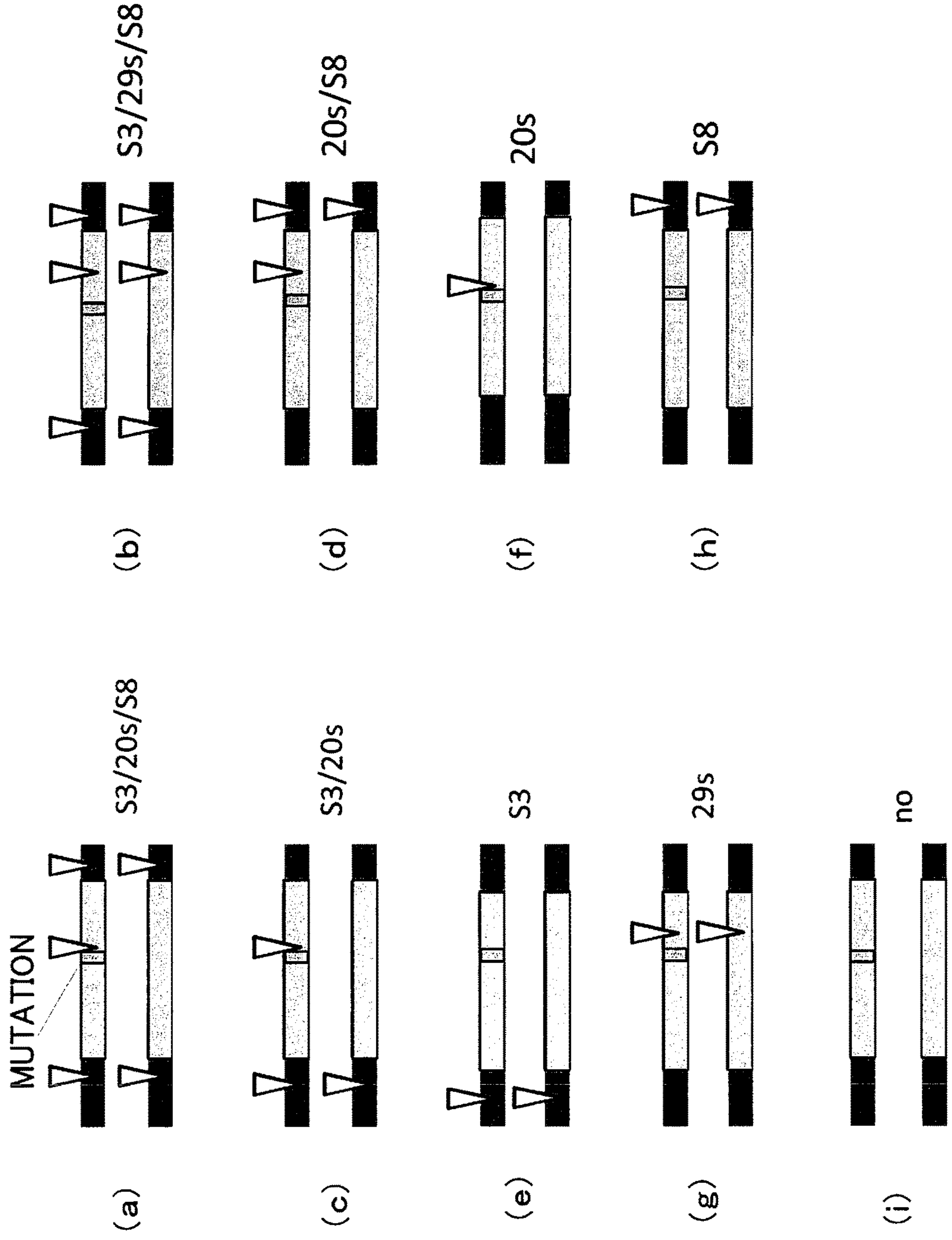
FIG. 12 shows the position where a single-strand break of DNA is inserted in each sample of the present example.

S3/20s/S8: 0.3 μL at 100 μM each
S3/29s/S8: 0.3 μL at 100 μM each
S3/20s: 0.45 μL at 100 μM each
20s/S8: 0.45 μL at 100 μM each
S3/S8: 0.45 μL at 100 μM each
S3: 0.9 μL at 100 μM
20s: 0.9 μL at 100 μM
29s: 0.9 μL at 100 μM
S8: 0.9 μL at 100 μM
no: 0.9 μL at 100 μM In addition, the position where a nick is inserted in each sample is shown in FIG. 12. In each sample, the cutting pattern (see FIGS. 1A to H) is as follows.

S3/20s/S8: pattern 5
S3/29s/S8: pattern 6
S3/20s: pattern 2(*a*)
20s/S8: pattern 4(*b*)
S3/S8: pattern 1
S3: nick was at one site each for the base of the donor allele and the corresponding base of the recipient allele
20s: nick at only one site
29s: nick was at one site each for the base of the donor allele and the corresponding base of the recipient allele
S8: nick was at one site each for the base of the donor allele and the corresponding base of the recipient allele
no: no nick generated B. Methods and Results Each sgRNA in the volume shown in the above list, 1.8 μL of Cas9 mRNA (500 ng/μL), and R buffer (INVITROGEN™ NEON™ Transfection Kit) were added to $70\times10^4$ TSCER2 cells to a total amount of 14 μL. Then, 10 μL of which was electroporated by NEON™ Transfection System under the condition of 1500 V for 10 ms 3 times (electroporation condition 3). After overnight culture at 37° C. 5% CO2 in 10% horse serum/RPMI1640 medium, culture was performed in 5% horse serum/RPMI1640 medium. One week after electroporation, some of the cells were transferred to CHAT medium (10 μM 2-deoxycytidine [Sigma], 200 μM hypoxanthine [Sigma], 100 nM aminopterin [Sigma], and 17.5 μM thymidine [Sigma]), dispensed into 96 plates so as to have 10, 30, 100, or 200 cells per well, and the culture was continued. In addition, for the measurement of plating efficiency, the cells in 5% horse serum-RPMI1640 medium were dispensed into 96 plates so as to have 1 cell per well, and cultured. After 2 to 3 weeks, the percentage of wells that had formed colonies was measured.

Figure 11:
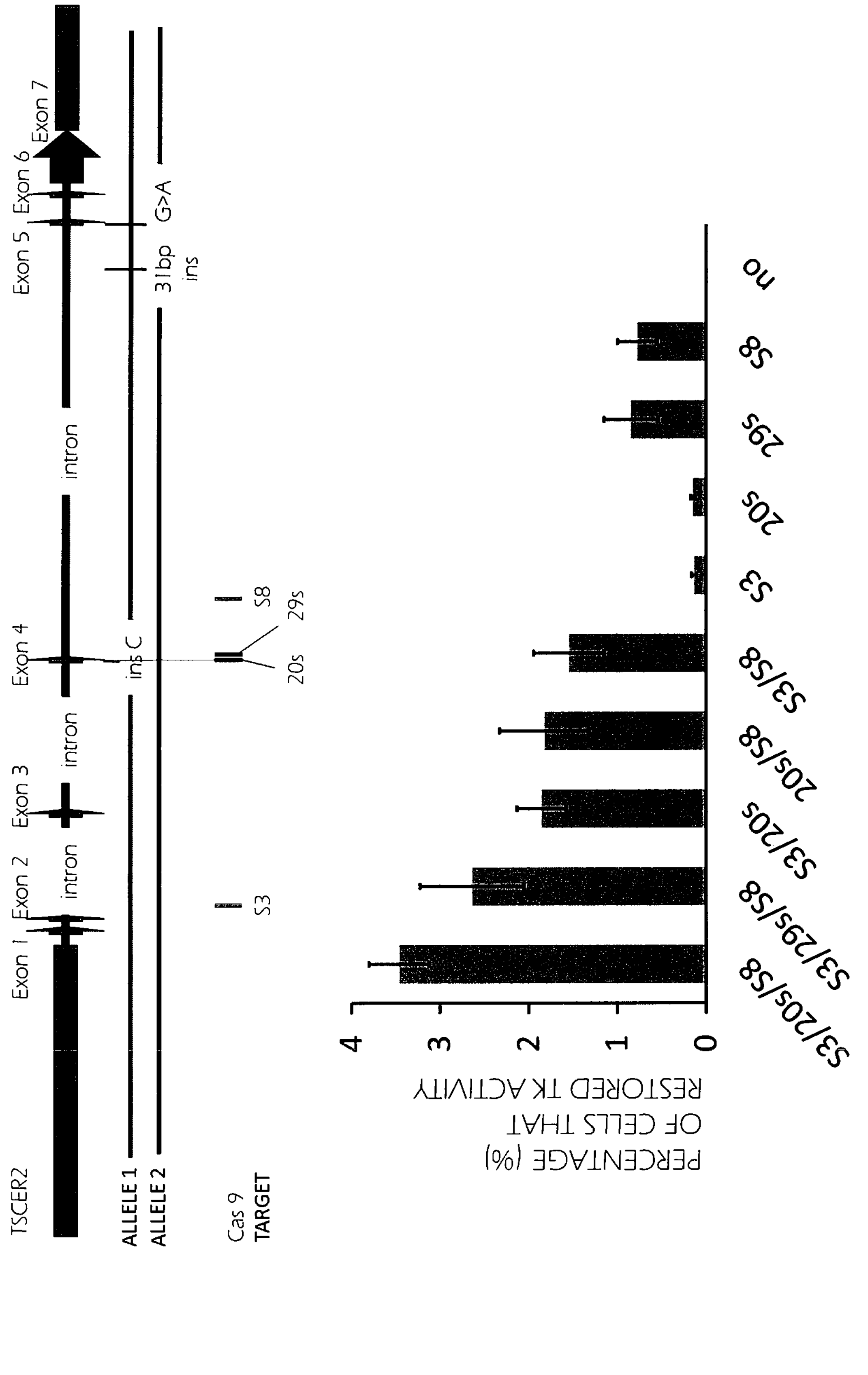
FIG. 11 shows the positions (upper part of the figure) where single-strand breaks of DNA are inserted in each sample of the present example shown in FIG. 12, and the results (lower part of the figure) of detecting cells in which genome editing took place using the recovery of thymidine kinase activity as an index.

The results are shown in FIG. 11. In sample S3/20s/S8 (pattern 5 of FIG. 1G), which has nicks at three sites in the recipient allele and two sites in the donor allele, under the condition that no exogenous DNA was used and cells were not selected by the cell sorter, the thymidine kinase activity was restored with a high efficiency of 3.46±0.34%. Also in sample S3/29s/S8 (pattern 6 of FIG. 1G), which has nicks at three sites in the recipient allele and three sites in the donor allele, the thymidine kinase activity was restored in 2.64±0.58% of the cells. Further, in sample S3/S8 (pattern 1 of FIG. 1A), which has nicks at two sites in the recipient allele and two sites in the donor allele at a position where nicks are 1000 bp or more away from the target nucleotide, the thymidine kinase activity was restored with higher efficiency at 1.54±0.40% than in samples S3 (0.133±0.026%), 29s (0.844±0.305%), and S8 (0.773±0.221%), which have nicks at one site in the recipient allele and one site in the donor allele, and in sample 20s (0.147±0.022%), which has a nick at one site in the recipient allele and no nick in the donor allele.

INDUSTRIAL APPLICABILITY

As described above, the present invention is capable of unifying different bases between homologous chromosomes into any of the bases by utilizing homologous recombination between homologous chromosomes induced by single-strand breaks with site-specific nickase. The present invention, which does not use exogenous donor DNA, can greatly contribute to gene therapy particularly for diseases caused by heterozygous mutations due to its high safety.

The invention claimed is:

1. A method for producing a genome-edited cell, comprising:

introducing, into a cell having homologous chromosomes, said homologous chromosomes comprising a donor homologous chromosome having a first base at a target site and a recipient homologous chromosome having a second base at a target site corresponding to the target site of the donor homologous chromosome, wherein the second base of the recipient homologous chromosome differs from the first base of the donor homologous chromosome, a combination of site-specific nickases, to result in a substitution of the second base of the recipient homologous chromosome with the first base of the donor homologous chromosome by homologous recombination of the donor homologous chromosome and the recipient homologous chromosome in the cell, wherein the combination of site-specific nickases cleaves a single strand in a neighboring DNA region of the target site of the donor homologous chromosome and a single strand in a neighboring DNA region of the target site of the recipient homologous chromosome, and the cleavage by the combination of site-specific nickases in the neighboring DNA region of the recipient homologous chromosome is at multiple sites in the neighboring DNA region, and the cleavage by the combination of site-specific nickases in the neighboring DNA region of the donor homologous chromosome is at least one of multiple sites corresponding to the multiple sites of single-strand breaks in the recipient homologous chromosome.

2. The method according to claim 1, wherein the second base of the recipient homologous chromosome is a mutant base and the first base of the donor homologous chromosome is a normal base.

3. The method according to claim 1, wherein the site-specific nickases are a CRISPR-Cas system.

4. A kit for use in the method according to claim 1, comprising:

a combination of site-specific nickases that cleaves, in a cell having homologous chromosomes, said homologous chromosomes comprising a donor homologous chromosome having a first base at a target site and a recipient homologous chromosome having a second base at a target site corresponding to the target site of the donor homologous chromosome, wherein the second base of the recipient homologous chromosome differs from the first base of the donor homologous chromosome, a single strand in a neighboring DNA region of the target site of the donor homologous chromosome and a single strand in a neighboring DNA region of the target site of the recipient homologous chromosome, wherein the cleavage by the combination of site-specific nickases in the neighboring DNA region of the recipient homologous chromosome is at multiple sites in the neighboring DNA region, and the cleavage by the combination of site-specific nickases in the neighboring DNA NBA-region of the donor homologous chromosome is at at least one of multiple sites corresponding to the multiple sites of single-strand breaks in the recipient homologous chromosome.

5. The kit according to claim 4, wherein the second base of the recipient homologous chromosome is a mutant base and the first base of the donor homologous chromosome is a normal base.

6. The kit according to claim 4, wherein the site-specific nickases are a CRISPR-Cas system.

* * * * *

SEQUENCE LISTING

<160> NUMBER OF SEQ ID NOS: 73

<210> SEQ ID NO 1
<211> LENGTH: 1540
<212> TYPE: DNA
<213> ORGANISM: Homo sapiens

<400> SEQUENCE: 1
gtgtctcgct gtgttaccca ggctggtctc gaactcctga gttcaagtga tcctcccgtc 60
ttggcctccc caaagattac gggcatgagc tgctgtgtct ggccagaata caggatttta 120
aaaatttatg ttttgcaaca taattaatat aaagacaaat ataacccagg cccagttcta 180
gttattcatt cttctgaatt ttaaaaggaa acatttggct ggcccctaat ggtatcatgg 240
gccctggtac ctgatgaagt tggcctagtc tgcccccagc tcctgaacag tggaagagtt 300

-continued

```
tttagtctca ttgagctttg tactggacat tactaatttc taatccaaag catcaagtga    360
agtggcttgt ataaataact ggttttcctc tgggaggcta aggcgggtgg atcacttaaa    420
agttaggagt ctgagaccag cctggccaac atggtgaaac cccatgtctg ctaaaaatac    480
aaaaattagc tgggtgtgat ggtgtgtgcc agtagtccca gctactcttg tggctgaggt    540
gggagaatcg cttgagaccc ttgagaattg ggaggtagag attgcaggga gccgagatgg    600
cgccactgca ctccagcctg ggtgacagag caagactctg tttcataaaa aataaataaa    660
taactggttt tctggacgag ggcctttccc ataggtgcta acttctcaaa gcccggctgg    720
gtgaacactg agcctgcttt gcaggtagca ggtggtcacg acagtgccat tccctggccc    780
ctgcattgtg gcttctggcc tccctggccc tgctcacgct ctggctttct cttcccagga    840
acaccatgga ggcactgccc gcctgcctgc tccgagacgt ggcccaggag gccctgggcg    900
tggctgtcat aggcatcgac gaggggcagt ttgtaagttg gcttgtcttg gcatcactct    960
tcctgccagc ttccgctctg tcctcccgtt ttccctcgct gacttggaag ttatctgatc   1020
ttttagtaaa ataacaaggt taaatagcta caactagtgt tggaataccc tctgaaggcc   1080
cctttctagt ttccctgtca tagtgtcata gtcttgtagg attcgtttta cttttttttt   1140
tttttttttg agacggagtt ttgctcttgt tgcccaggcc ggagtacgat ggcacaatct   1200
caccgcaaac tttgcttcct gggttcaagc aattctctcc tgtctcagcc tcccgagtag   1260
ctgggattac aggcatgcgc caccacgccc agctaatttt atatttttag tagagatggg   1320
gtttctccat gttggtcaag ctggtctcaa actcccaacc tcaggtgatc cgccccgcct   1380
tgaactccca aagcgctggg attacaggca tgagctacca cacctggcca ttgtaccttt   1440
ttaaaaatac atatatctat ttactggcaa gatgcagtga ctcacacctg taatctcagc   1500
ctgtgggagg ccaaggtgga cagatcactt gagcccagga                         1540
```

<210> SEQ ID NO 2
<211> LENGTH: 1541
<212> TYPE: DNA
<213> ORGANISM: Homo sapiens

<400> SEQUENCE: 2

```
gtgtctcgct gtgttaccca ggctggtctc gaactcctga gttcaagtga tcctcccgtc     60
ttggcctccc caaagattac gggcatgagc tgctgtgtct ggccagaata caggatttta    120
aaaatttatg ttttgcaaca taattaatat aaagacaaat ataacccagg cccagttcta    180
gttattcatt cttctgaatt ttaaaaggaa acatttggct ggcccctaat ggtatcatgg    240
gccctggtac ctgatgaagt tggcctagtc tgcccccagc tcctgaacag tggaagagtt    300
tttagtctca ttgagctttg tactggacat tactaatttc taatccaaag catcaagtga    360
agtggcttgt ataaataact ggttttcctc tgggaggcta aggcgggtgg atcacttaaa    420
agttaggagt ctgagaccag cctggccaac atggtgaaac cccatgtctg ctaaaaatac    480
aaaaattagc tgggtgtgat ggtgtgtgcc agtagtccca gctactcttg tggctgaggt    540
gggagaatcg cttgagaccc ttgagaattg ggaggtagag attgcaggga gccgagatgg    600
cgccactgca ctccagcctg ggtgacagag caagactctg tttcataaaa aataaataaa    660
taactggttt tctggacgag ggcctttccc ataggtgcta acttctcaaa gcccggctgg    720
gtgaacactg agcctgcttt gcaggtagca ggtggtcacg acagtgccat tccctggccc    780
ctgcattgtg gcttctggcc tccctggccc tgctcacgct ctggctttct cttcccagga    840
acaccatgga ggcactgccc cgcctgcctg ctccgagacg tggcccagga ggccctgggc    900
```

gtggctgtca taggcatcga cgaggggcag tttgtaagtt ggcttgtctt ggcatcactc 960
ttcctgccag cttccgctct gtcctcccgt tttccctcgc tgacttggaa gttatctgat 1020
cttttagtaa aataacaagg ttaaatagct acaactagtg ttggaatacc ctctgaaggc 1080
ccctttctag tttccctgtc atagtgtcat agtcttgtag gattcgtttt actttttttt 1140
tttttttttt gagacggagt tttgctcttg ttgcccaggc cggagtacga tggcacaatc 1200
tcaccgcaaa ctttgcttcc tgggttcaag caattctctc ctgtctcagc ctcccgagta 1260
gctgggatta caggcatgcg ccaccacgcc cagctaattt tatattttta gtagagatgg 1320
ggtttctcca tgttggtcaa gctggtctca aactcccaac ctcaggtgat ccgccccgcc 1380
ttgaactccc aaagcgctgg gattacaggc atgagctacc acacctggcc attgtacctt 1440
tttaaaaata catatatcta tttactggca agatgcagtg actcacacct gtaatctcag 1500
cctgtgggag gccaaggtgg acagatcact tgagcccagg a 1541

<210> SEQ ID NO 3
<211> LENGTH: 323
<212> TYPE: DNA
<213> ORGANISM: Homo sapiens

<400> SEQUENCE: 3
tactgattct ccagctcctg cagggcacaa acatgaggct ccgtaagact ttccttctca 60
acagagtgtg cccctccccc tcgcccatgc ccggctgctc ctctctgcct tagaagccct 120
cgccccagta tcccagggtc tccaagatgc cctcagatcc atggtctaga ggtataccag 180
cgaccgctgt gcctttagcc agctggcagc cttaagggga gatgaggtcc cccaaacgaa 240
ttcagttaat gccatcatgg gcaccactcc cacagcagtt acgaccaggg gaggccaggt 300
ggcccggtgg ctcacgcctg taa 323

<210> SEQ ID NO 4
<211> LENGTH: 324
<212> TYPE: DNA
<213> ORGANISM: Homo sapiens

<400> SEQUENCE: 4
agccgagatc atgccactgc actccagcct gggtgactga gcgagactgt gtctcaaaaa 60
aagaaggcat gtatccaaat cacaaggtta aaagagataa agcatgcgag taaaataaag 120
caagccagtc agtgtgggtt gcttcttcct cccagtgaag gagctctttg tcagaggtcc 180
ttggatctgt ccaatctgta cctggaaagg ttattacctg taggatcctt acagccacac 240
ctggcacact ctgtgatcac taccaccatc tttgttgcta ttatttatga tcatgattat 300
acaatgggtt tcttttcttt cttt 324

<210> SEQ ID NO 5
<211> LENGTH: 324
<212> TYPE: DNA
<213> ORGANISM: Homo sapiens

<400> SEQUENCE: 5
ttcgcggggc tggggtggag ctccttcctc ttctccgggg accccttgtc ccgtccctcc 60
cctccccttc cctcccctcc cctcccctcc ccttcccttc cctccccttc ccttccccta 120
gaaggaccag cacagcctcc tacagctccc gcctggggtg ctcctccctt gaattcagtc 180
caggaggaag tctctgccct cttctgccca ggccaagccc ctcgtcctgt gtggacgcca 240

-continued

```
ctccctcctg gagctggtga cagctgctta cagcttagct gtcttcccca ccaagtcctc    300

tgagaaggtg gcaaccagtt gtgt                                           324


<210> SEQ ID NO 6
<211> LENGTH: 324
<212> TYPE: DNA
<213> ORGANISM: Homo sapiens

<400> SEQUENCE: 6

cctctctcct cttgcagcac agagttgatg agacgcgtcc gtcgcttcca gattgctcag     60

tacaagtgcc tggtgatcaa gtatgccaaa gacactcgct acagcagcag cttctgcaca    120

catgaccggt cagtccctgc cccctgcagt cctgtccagt ggaaaatcac aaggcacagg    180

acacactgtt aggactctct ttaatgggga tggttaatca tttgaacatt gaatgattca    240

aatcagcaca ctttccaagg tgcttggcaa ggtagcgcac actctccact ccctgggctg    300

gagccagtgg ttctccactg aggg                                           324


<210> SEQ ID NO 7
<211> LENGTH: 324
<212> TYPE: DNA
<213> ORGANISM: Homo sapiens

<400> SEQUENCE: 7

gggaatttaa ccgcacttcg tgaccatgct gtctgatgta ggtcatttac ttttccaaat     60

ttgcttcctc attcctaaga tgcgatgtcc acggcacagg gtggtgttac acctggtggg    120

gacagggaaa gcagaggagg tcacttcgtt ccagctgttg gaagtacaac ttctggagtc    180

agtcagatcc gggattaaat atgagttctg cccgtgtgtc acaagtcatc tctaacacgg    240

gccacagagg ccaaggctgg gccagcagca ttgatggctc gagaggctgc ccttgcaggg    300

gccacagctg gcctcccacc tgcc                                           324


<210> SEQ ID NO 8
<211> LENGTH: 325
<212> TYPE: DNA
<213> ORGANISM: Homo sapiens

<400> SEQUENCE: 8

ctggccagaa tacaggattt taaaaattta tgttttgcaa cataattaat ataaagacaa     60

atataaccca ggcccagttc tagttattca ttcttctgaa ttttaaaagg aaacatttgg    120

ctggccccta atggtatcat gggccctggt acctgatgaa gttggcctag tctgccccca    180

gctcctgaac agtggaagag tttttagtct cattgagctt tgtactggac attactaatt    240

tctaatccaa agcatcaagt gaagtggctt gtataaataa ctggttttcc tctgggaggc    300

taaggcgggt ggatcactta aaagt                                          325


<210> SEQ ID NO 9
<211> LENGTH: 324
<212> TYPE: DNA
<213> ORGANISM: Homo sapiens

<400> SEQUENCE: 9

accatggagg cactgccccg cctgcctgct ccgagacgtg gcccaggagg ccctgggcgt     60

ggctgtcata ggcatcgacg aggggcagtt tgtaagttgg cttgtcttgg catcactctt    120

cctgccagct tccgctctgt cctcccgttt tccctcgctg acttggaagt tatctgatct    180

tttagtaaaa taacaaggtt aaatagctac aactagtgtt ggaataccct ctgaaggccc    240
```

ctttctagtt tccctgtcat agtgtcatag tcttgtagga ttcgttttac ttttttttt 300 ttttttttga gacggagttt tgct 324

<210> SEQ ID NO 10
<211> LENGTH: 324
<212> TYPE: DNA
<213> ORGANISM: Homo sapiens

<400> SEQUENCE: 10
actccagccc gggcgacaag gccagaccct gtctcaaaaa aaaaaggggg aggtggggag 60
taatgtttgg tttgcctcat ggttcctttt gcttgtttct tatacgttta ttttcttgtt 120
gttgaagtac ctttttagt agtttttgca gccaggaggt atagatggga agctgccagt 180
ctttgtatgg aaatctttct tttgtcatct agtttaagct gggcagcaag aggtaggttg 240
atcttgtgtg ggtttgggtt ttttttttt ttttgagacg gagtcttact ctgtcgccca 300
ggctggagtg caatggcgtg atct 324

<210> SEQ ID NO 11
<211> LENGTH: 324
<212> TYPE: DNA
<213> ORGANISM: Homo sapiens

<400> SEQUENCE: 11
tttgttagtt tatcacaaag aatgaaactg aaactctctc caaggggttt agcagacttg 60
acctcttagg tacttttagg gttgcctcga agtacacaat gtggtggttt gatataaaca 120
taacaggaat ttatttctcg ctcacagacc ccctacgtgg ttccaggccg gttgatgggg 180
aggccgccca cgaggcggct taggtcgccc tggctggctg tatacagaca cggaggggaa 240
gagacgtggc ggagcccctg ggtgtgaggt tttcatgggc ctgaccagaa gctgcaaacg 300
tcacttctgc tgatctttca aaga 324

<210> SEQ ID NO 12
<211> LENGTH: 324
<212> TYPE: DNA
<213> ORGANISM: Homo sapiens

<400> SEQUENCE: 12
tacttgggag gctgaggcag gagaatcgct tgaacccggt aggcgaaggt tgcagtgagc 60
caagatcgcc ccattgcact ccaagcctgg gcaacaacaa gagcaaaact cagtctcaaa 120
acaaaacaaa acaaaagaag ttcagggtct tcccattgca agcagttcta gatcgaggag 180
aggggttcct agcatgggac ccagcagaag gactgtcctt cgctccttca ttgtctacgt 240
ggacagtgga tgaagcccag ccgaacctgc cttgttcccg ttttctgggt cagcagggaa 300
agcctttcac agagtagcca ccgt 324

<210> SEQ ID NO 13
<211> LENGTH: 324
<212> TYPE: DNA
<213> ORGANISM: Homo sapiens

<400> SEQUENCE: 13
accttgctaa gccctcacgt ctcaataacc tcaaacctca gtacctgggc tgagaaagcc 60
tgagtggccc tgggagagag accctgcacc caaggacaag gacatccctg cttcacccaa 120
cccaaaggcc agtctggaca tatgaactca accagctaag agtgatatga ttgattgatg 180

-continued

```
agaatcacca gagcacttgc cagagtttca gcttctccct gggccaaagt gaagtttgct    240

ttacacagta aatgtgctct gtgcaggtcc tgaatttaga aggctgtgct gtgtcatcct    300

gctctgtaaa tggccagtag gacc                                            324


<210> SEQ ID NO 14
<211> LENGTH: 324
<212> TYPE: DNA
<213> ORGANISM: Homo sapiens

<400> SEQUENCE: 14

ggtggcacca accttgctgg gacttggatc ccaggggctt atctcttcaa gtgtggagag     60

ggcagggtcc acgcctctgc tgtagcttat gaaattaact aattgaaaat tcactggttg    120

gtggacgcac atttctcttt cacctgggtt tccctgggtc tcatggacag ctccaacttg    180

atttgggtgg ggattttctt ccagatcttt ttttcttttg ttttgagaca gggtctctgt    240

cgcccaggct ggagtgcagt gacgcaatcc ctgctcactg cagcctctgc ttccccagtt    300

gaagtgattc tcccccgtca gcct                                            324


<210> SEQ ID NO 15
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1(ex4)20s

<400> SEQUENCE: 15

cgtctcggag caggcaggcg ggg                                              23


<210> SEQ ID NO 16
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1(ex4)21s

<400> SEQUENCE: 16

acgtctcgga gcaggcaggc ggg                                              23


<210> SEQ ID NO 17
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1(ex4)-
      322s

<400> SEQUENCE: 17

cctcagccac aagagtagct ggg                                              23


<210> SEQ ID NO 18
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1(ex4)29s

<400> SEQUENCE: 18

cctgggccac gtctcggagc agg                                              23


<210> SEQ ID NO 19
<211> LENGTH: 23
<212> TYPE: DNA
```

-continued

<213> ORGANISM: Artificial Sequence
<220> FEATURE:
<223> OTHER INFORMATION: Synthetic sequence, crRNA of TSCER2_TK1_S1

<400> SEQUENCE: 19
acctctagac catggatctg agg 23

<210> SEQ ID NO 20
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S2

<400> SEQUENCE: 20
ctgacaaaga gctccttcac tgg 23

<210> SEQ ID NO 21
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S3

<400> SEQUENCE: 21
attcaaggga ggagcacccc agg 23

<210> SEQ ID NO 22
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S4

<400> SEQUENCE: 22
cttgtgattt tccactggac agg 23

<210> SEQ ID NO 23
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S5

<400> SEQUENCE: 23
gaagttgtac ttccaacagc tgg 23

<210> SEQ ID NO 24
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S6

<400> SEQUENCE: 24
cagactaggc caacttcatc agg 23

<210> SEQ ID NO 25
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S7

<400> SEQUENCE: 25
gataacttcc aagtcagcga ggg 23

-continued

<210> SEQ ID NO 26
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S8

<400> SEQUENCE: 26
agcttcccat ctatacctcc tgg 23

<210> SEQ ID NO 27
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S9

<400> SEQUENCE: 27
caaccggcct ggaaccacgt agg 23

<210> SEQ ID NO 28
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S10

<400> SEQUENCE: 28
gatctagaac tgcttgcaat ggg 23

<210> SEQ ID NO 29
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S11

<400> SEQUENCE: 29
tcaatcatat cactcttagc tgg 23

<210> SEQ ID NO 30
<211> LENGTH: 23
<212> TYPE: DNA
<213> ORGANISM: Artificial Sequence
<220> FEATURE:
<223> OTHER INFORMATION: Synthetic sequence, crRNA of TSCER2_TK1_S12

<400> SEQUENCE: 30
ggagctgtcc atgagaccca ggg 23

<210> SEQ ID NO 31
<211> LENGTH: 25
<212> TYPE: DNA
<213> ORGANISM: Artificial Sequence
<220> FEATURE:
<223> OTHER INFORMATION: Synthetic sequence, primer sequence

<400> SEQUENCE: 31
tcctgaacag tggaagagtt tttag 25

<210> SEQ ID NO 32
<211> LENGTH: 22
<212> TYPE: DNA
<213> ORGANISM: Artificial Sequence
<220> FEATURE:

-continued

<223> OTHER INFORMATION: Synthetic sequence, primer sequence

<400> SEQUENCE: 32
aacttacaaa ctgcccctcg tc 22

<210> SEQ ID NO 33
<211> LENGTH: 18
<212> TYPE: DNA
<213> ORGANISM: Artificial Sequence
<220> FEATURE:
<223> OTHER INFORMATION: Synthetic sequence, primer sequence

<400> SEQUENCE: 33
tgaacactga gcctgctt 18

<210> SEQ ID NO 34
<211> LENGTH: 23
<212> TYPE: DNA
<213> ORGANISM: Artificial Sequence
<220> FEATURE:
<223> OTHER INFORMATION: Synthetic sequence, primer sequence

<400> SEQUENCE: 34
agttgtggat gtacctgtcg tct 23

<210> SEQ ID NO 35
<211> LENGTH: 20
<212> TYPE: DNA
<213> ORGANISM: Artificial Sequence
<220> FEATURE:
<223> OTHER INFORMATION: Synthetic sequence, primer sequence

<400> SEQUENCE: 35
atgcccggct ctgtcccttt 20

<210> SEQ ID NO 36
<211> LENGTH: 18
<212> TYPE: DNA
<213> ORGANISM: Artificial Sequence
<220> FEATURE:
<223> OTHER INFORMATION: Synthetic sequence, primer sequence

<400> SEQUENCE: 36
taaccctgtg gtggctga 18

<210> SEQ ID NO 37
<211> LENGTH: 17
<212> TYPE: DNA
<213> ORGANISM: Homo sapiens

<400> SEQUENCE: 37
ctgcctgctc cgagacg 17

<210> SEQ ID NO 38
<211> LENGTH: 17
<212> TYPE: DNA
<213> ORGANISM: Homo sapiens

<400> SEQUENCE: 38
tgcctgctcc gagacgt 17

<210> SEQ ID NO 39
<211> LENGTH: 17
<212> TYPE: DNA
<213> ORGANISM: Homo sapiens

<400> SEQUENCE: 39
tactcttgtg gctgagg 17

<210> SEQ ID NO 40
<211> LENGTH: 17
<212> TYPE: DNA
<213> ORGANISM: Homo sapiens

<400> SEQUENCE: 40
ccgagacgtg gcccagg 17

<210> SEQ ID NO 41
<211> LENGTH: 17
<212> TYPE: DNA
<213> ORGANISM: Homo sapiens

<400> SEQUENCE: 41
atccatggtc tagaggt 17

<210> SEQ ID NO 42
<211> LENGTH: 17
<212> TYPE: DNA
<213> ORGANISM: Homo sapiens

<400> SEQUENCE: 42
aaggagctct ttgtcag 17

<210> SEQ ID NO 43
<211> LENGTH: 17
<212> TYPE: DNA
<213> ORGANISM: Homo sapiens

<400> SEQUENCE: 43
gtgctcctcc cttgaat 17

<210> SEQ ID NO 44
<211> LENGTH: 17
<212> TYPE: DNA
<213> ORGANISM: Homo sapiens

<400> SEQUENCE: 44
cagtggaaaa tcacaag 17

<210> SEQ ID NO 45
<211> LENGTH: 17
<212> TYPE: DNA
<213> ORGANISM: Homo sapiens

<400> SEQUENCE: 45
gttggaagta caacttc 17

<210> SEQ ID NO 46
<211> LENGTH: 17
<212> TYPE: DNA
<213> ORGANISM: Homo sapiens

<400> SEQUENCE: 46
gaagttggcc tagtctg 17

<210> SEQ ID NO 47
<211> LENGTH: 17
<212> TYPE: DNA

-continued

<213> ORGANISM: Homo sapiens

<400> SEQUENCE: 47
ctgacttgga agttatc 17

<210> SEQ ID NO 48
<211> LENGTH: 17
<212> TYPE: DNA
<213> ORGANISM: Homo sapiens

<400> SEQUENCE: 48
ggtatagatg ggaagct 17

<210> SEQ ID NO 49
<211> LENGTH: 17
<212> TYPE: DNA
<213> ORGANISM: Homo sapiens

<400> SEQUENCE: 49
tggttccagg ccggttg 17

<210> SEQ ID NO 50
<211> LENGTH: 17
<212> TYPE: DNA
<213> ORGANISM: Homo sapiens

<400> SEQUENCE: 50
gcaagcagtt ctagatc 17

<210> SEQ ID NO 51
<211> LENGTH: 17
<212> TYPE: DNA
<213> ORGANISM: Homo sapiens

<400> SEQUENCE: 51
aagagtgata tgattga 17

<210> SEQ ID NO 52
<211> LENGTH: 17
<212> TYPE: DNA
<213> ORGANISM: Homo sapiens

<400> SEQUENCE: 52
gtctcatgga cagctcc 17

<210> SEQ ID NO 53
<211> LENGTH: 23
<212> TYPE: DNA
<213> ORGANISM: Homo sapiens

<400> SEQUENCE: 53
ccccgcctgc ctgctccgag acg 23

<210> SEQ ID NO 54
<211> LENGTH: 22
<212> TYPE: DNA
<213> ORGANISM: Homo sapiens

<400> SEQUENCE: 54
cccgcctgcc tgctccgaga cg 22

<210> SEQ ID NO 55
<211> LENGTH: 22

<212> TYPE: DNA
<213> ORGANISM: Homo sapiens

<400> SEQUENCE: 55
ccccgctgcc tgctccgaga cg 22

<210> SEQ ID NO 56
<211> LENGTH: 22
<212> TYPE: DNA
<213> ORGANISM: Homo sapiens

<400> SEQUENCE: 56
ccccgccgcc tgctccgaga cg 22

<210> SEQ ID NO 57
<211> LENGTH: 23
<212> TYPE: DNA
<213> ORGANISM: Homo sapiens

<400> SEQUENCE: 57
ccccgcctgc ctgctccgag acg 23

<210> SEQ ID NO 58
<211> LENGTH: 23
<212> TYPE: DNA
<213> ORGANISM: Homo sapiens

<400> SEQUENCE: 58
cccgcctgcc tgctccgaga cgc 23

<210> SEQ ID NO 59
<211> LENGTH: 23
<212> TYPE: DNA
<213> ORGANISM: Homo sapiens

<400> SEQUENCE: 59
ccccgcctgc ctgctccgag acg 23

<210> SEQ ID NO 60
<211> LENGTH: 22
<212> TYPE: DNA
<213> ORGANISM: Homo sapiens

<400> SEQUENCE: 60
cccgcctgcc tgctccgaga cg 22

<210> SEQ ID NO 61
<211> LENGTH: 39
<212> TYPE: DNA
<213> ORGANISM: Homo sapiens

<400> SEQUENCE: 61
tgccccgcct gcctgctccg agacgtggcc caggaggcc 39

<210> SEQ ID NO 62
<211> LENGTH: 39
<212> TYPE: DNA
<213> ORGANISM: Homo sapiens

<400> SEQUENCE: 62
tgcccgcctg cctgctccga gacgtggccc aggaggccc 39

<210> SEQ ID NO 63

<211> LENGTH: 39
<212> TYPE: DNA
<213> ORGANISM: Homo sapiens

<400> SEQUENCE: 63
tgcccgcctg cctgctccga gacgtggccc aggaggccc 39

<210> SEQ ID NO 64
<211> LENGTH: 39
<212> TYPE: DNA
<213> ORGANISM: Homo sapiens

<400> SEQUENCE: 64
tgccccgctg cctgctccga gacgtggccc aggaggccc 39

<210> SEQ ID NO 65
<211> LENGTH: 39
<212> TYPE: DNA
<213> ORGANISM: Homo sapiens

<400> SEQUENCE: 65
tgcccgcctg cctgctccga gacgtggccc aggaggccc 39

<210> SEQ ID NO 66
<211> LENGTH: 39
<212> TYPE: DNA
<213> ORGANISM: Homo sapiens

<400> SEQUENCE: 66
tgccccgccg cctgctccga gacgtggccc aggaggccc 39

<210> SEQ ID NO 67
<211> LENGTH: 39
<212> TYPE: DNA
<213> ORGANISM: Homo sapiens

<400> SEQUENCE: 67
tgcccgcctg cctgctccga gacgtggccc aggaggccc 39

<210> SEQ ID NO 68
<211> LENGTH: 78
<212> TYPE: DNA
<213> ORGANISM: Homo sapiens

<400> SEQUENCE: 68
gttggccatg gcctcgtaga actccacgat gtcagggaac tggaaagggc acgtggagaa 60
agagtgtgag agcttcca 78

<210> SEQ ID NO 69
<211> LENGTH: 78
<212> TYPE: DNA
<213> ORGANISM: Homo sapiens

<400> SEQUENCE: 69
gttggccatg gcctcgcaga actccacgat gtcagggaac tggaaagggc acgtggagaa 60
agagtgtgag agcttcca 78

<210> SEQ ID NO 70
<211> LENGTH: 79
<212> TYPE: DNA
<213> ORGANISM: Homo sapiens -continued

```
<400> SEQUENCE: 70

ccccagcagc agctccctgg agccccagcg aagacgctgc cagatcctcg agagtaggga     60

taacagggta atggatctg                                                  79


<210> SEQ ID NO 71
<211> LENGTH: 79
<212> TYPE: DNA
<213> ORGANISM: Homo sapiens

<400> SEQUENCE: 71

ccccagcagc agctccctgg agccccagcg aagacgctgc cagatctgac aactccggcc     60

atttggcccg gagtaactc                                                  79


<210> SEQ ID NO 72
<211> LENGTH: 78
<212> TYPE: DNA
<213> ORGANISM: Homo sapiens

<400> SEQUENCE: 72

gttggccatg gcctcgcaga actccacgat gtcagggaac tggaaagggc acgtggagaa     60

agagtgtgag agcttcca                                                   78


<210> SEQ ID NO 73
<211> LENGTH: 79
<212> TYPE: DNA
<213> ORGANISM: Homo sapiens

<400> SEQUENCE: 73

ccccagcagc agctccctgg agccccagcg aagacgctgc cagatctgac aactccggcc     60

atttggcccg gagtaactc                                                  79
```